United States Patent [19]

Ikegami et al.

[11] Patent Number: 5,723,327

[45] Date of Patent: *Mar. 3, 1998

[54] THERMOSTABLE TREHALOSE-RELEASING ENZYME, AND ITS PREPARATION AND USES

[75] Inventors: Shouji Ikegami; Michio Kubota; Toshiyuki Sugimoto; Toshio Miyake, all of Okayama, Japan

[73] Assignee: Kabushiki Kaisha Hayashibara Seibutsu Kagaku Kenkyujo, Okayama, Japan

[*] Notice: The term of this patent shall not extend beyond the expiration date of Pat. Nos. 5,455,168 and 5,472,863.

[21] Appl. No.: 485,132

[22] Filed: Jun. 7, 1995

[30] Foreign Application Priority Data

Jun. 25, 1994 [JP] Japan ................................. 6-166126
Apr. 11, 1995 [JP] Japan ................................. 7-109130

[51] Int. Cl.$^6$ ............................. C12N 9/26; C12D 19/12; C13K 13/00
[52] U.S. Cl. ......................... 435/201; 435/200; 435/193; 435/195; 435/100; 536/123.13
[58] Field of Search .......................... 435/207, 200, 435/193, 195, 100; 536/123.13

[56] References Cited

U.S. PATENT DOCUMENTS

| | | | |
|---|---|---|---|
| 4,521,252 | 6/1985 | Miyake et al. | 127/46.3 |
| 4,762,857 | 8/1988 | Bollin, Jr. et al. | 514/777 |
| 4,839,164 | 6/1989 | Smith | 424/64 |
| 5,026,566 | 6/1991 | Roser | 426/443 |
| 5,455,168 | 10/1995 | Maruta et al. | 435/201 |
| 5,472,863 | 12/1995 | Maruta et al. | 435/200 |

FOREIGN PATENT DOCUMENTS

| | | |
|---|---|---|
| 0 600 730 A1 | 6/1994 | European Pat. Off. . |
| 50-154485 | 12/1975 | Japan . |
| 58-23799 | 2/1983 | Japan . |
| 58-72598 | 4/1983 | Japan . |
| 58-216695 | 12/1983 | Japan . |
| 2106912 | 4/1983 | United Kingdom . |

OTHER PUBLICATIONS

"Catalogue of Bacteria and Phages", Amer. Type Cult. Collec., 18th Edit., p. 363,(1992).

Handbook of Amylases and Related Enzymes, Their Sources, Isolation Methods, Properties and Applications, pp.18–63, Wheaton & Co., Ltd. (press) (1988).

Lama, L. et al. "Starch Conversion With Immobilized Thermophilic Archaebacterium Sulfolobus Solfataricus" *Biotech. Ltrs.*, vol. 12, No. 6, pp. 431–432 (1990).

"Catalogue of Fungi/Yeasts, Amer. Type Cu.t. Collection", 17th Edit. p. 21 (1987).

Hoelzle, I. et al., "Increased Accumulation of Trehalose in Rhizobia Cultured Under 1% Oxygen", *Appl. Environ. Micro.*, p. 3213–3215, (1990).

Lama, L. et al. "Thermostable Amyulolytic Activity From Solfolobus Solfataricus", *BFE* vol. 8, No. 4, pp. 201–203, (1991).

Birch, G. "Trehaloses", *Adv. in Carbo. Chem.*, Acedemic Press, pp. 202–225, (1963).

ATCC Catalogue of Bacteria & Bacteriophages, 18th Ed., 1992, p. 363.

*Primary Examiner*—Leon B. Lankford, Jr.
*Assistant Examiner*—Francisco C. Prats
*Attorney, Agent, or Firm*—Browdy and Neimark

[57] ABSTRACT

Disclosed are novel thermostable trehalose-releasing enzyme, and its preparations and uses. The enzyme is obtainable from the culture of microorganisms such as *Sulfolobus acidocaldarius* (ATCC 33909 and ATCC 49426) and *Sulfolobus solfataricus* (ATCC 35091 and ATCC 35092), and capable of hydrolyzing at a temperature of over 55° C. the linkage between a trehalose moiety and the remaining glycosyl moiety in a non-reducing saccharide having a trehalose structure as an end unit and having a degree of glucose polymerization of 3 or higher. Trehalose and compositions containing the same are extensively useful in food products, cosmetics and pharmaceuticals.

15 Claims, 5 Drawing Sheets

THERMOSTABLE TREHALOSE-RELEASING ENZYME, AND ITS PREPARATION AND USES

BACKGROUND OF THE INVENTION

1. Field of the invention

The present invention relates to a thermostable trehalose-releasing enzyme, and its preparation and uses, more particularly, to a novel thermostable trehalose-releasing enzyme which specifically hydrolyses the linkage between a trehalose moiety and the remaining glycosyl moiety in non-reducing saccharides having a trehalose structure as an end unit and having a glucose polymerization degree of 3 or higher, and to the preparation of the enzyme. The present invention further relates to trehalose obtainable by using the enzyme and to compositions containing the same.

2. Description of the prior

Trehalose or α, α-trehalose is known as a non-reducing saccharide consisting of glucose units. As is described in *Advances in Carbohydrate Chemistry*, Vol. 18, pp. 201–225 (1963), published by Academic Press, USA, and *Applied and Environmental Microbiology*, Vol. 56, pp. 3,213–3,215 (1990), trehalose widely exists in microorganisms, mushrooms, insects, etc., though the content is relatively low. Trehalose is a non-reducing saccharide, so that it neither reacts with substances containing amino groups such as amino acids and proteins, induces the amino-carbonyl reaction, nor deteriorates amino acid-containing substances. Thus, trehalose is expected to be used without fear of causing an unsatisfactory browning and deterioration. Because of these, the establishment of the industrial-scale preparation of trehalose has been in great demand.

Conventional preparations of trehalose are, for example, those which are disclosed in Japanese Patent Laid-Open No. 154,485/75 wherein microorganisms are utilized, and reported in Japanese Patent Laid-Open No. 216,695/83 wherein maltose is converted into trehalose by using maltose- and trehalose-phosphorylases in combination. The former, however, is not suitable for industrial-scale preparation because the content of trehalose contained in microorganisms used as a starting material is usually lower than 15 w/w % (the wording "w/w %" will be abbreviated as "%" in the specification, unless otherwise specified), on a dry solid basis (d.s.b.), and the extraction and purification steps are complicated. The latter has the following demerits: (i) Since trehalose is formed via glucose-1-phosphate, the concentration of maltose as a substrate could not be set to a desired level; (ii) the enzymatic reaction systems of the phosphorylases are reversible reactions, and their yields of the objective trehalose are relatively low; and (iii) it is substantially difficult to retain their reaction systems stably and to continue their enzymatic reactions smoothly. Thus, these conventional preparations have not been actually used as an industrial-scale preparation.

Considering the aforementioned circumstances, the present inventors have energetically studied enzymes which are capable of forming saccharides having a trehalose structure when allowed to act on starch hydrolysates. As a result, the present inventors found that Rhizobium sp. M-11 or Arthrobactor sp. Q36 is capable of producing a novel non-reducing saccharide-forming enzyme which forms non-reducing saccharides having a trehalose structure as an end unit when allowed to act on reducing partial starch hydrolysates having a degree of glucose polymerization of 3 or higher, and simultaneously found that a trehalose-releasing enzyme produced by Rhizobium sp. M-11 or Arthrobactor sp. Q36 can hydrolyse the non-reducing saccharides into trehalose and glucose and/or maltooligosaccharide at a constant amount. These enzymes realized that an objective amount of trehalose can be readily obtained by using starch as a material, and the aforementioned object concerning a trehalose is expected to be attainable.

Enzymes derived from Rhizobium sp. M-11 or Arthrobactor sp. Q36, however, are relatively-low in thermal stability. Thus, in case that these enzymes are utilized for preparing trehalose and non-reducing saccharides having a trehalose structure as an end unit, it is necessary to allow the enzymes to act on at a temperature of below 55° C. With regard to the temperature of enzymatic reaction, as described in the column titled "Enzymes related to saccharides" in the chapter titled "Enzymes related to saccharides and their applications" in "*Koso-Ouyou-no-Chishiki*" (Knowledge on Enzyme Applications), the first edition, pp. 80–129 (1986) that "In the conditions of industrial-scale enzymatic reactions for saccharification, the reactions at a temperature of below 55° C. involves a risk of contamination and a decrease of pH during the reaction, in long-time enzymatic reactions using starch as a material, when an enzyme is allowed to act on at a temperature of below 55° C., because of contamination and a decrease of pH of reaction mixtures which inactivate the activity of such enzymes, and it is necessary to add lysozyme for the prevention of contamination and the pH control of the reaction mixtures. In addition, when the hydrolysis of partial starch hydrolysates is relatively low, insoluble substances may be formed due to retrogradation of starch.

On the other hand, since a thermostable enzyme can maintain its activity at a relatively-high temperature, contamination during the enzymatic reaction is less of a concern and the retrogradation of partial starch hydrolysates is scarcely caused. As a source of thermostable enzymes, thermophilic microorganisms can be generally considered. Regarding a preparation of trehalose using thermophilic microorganisms, as described in *Biotechnology Letters*, Vol. 12, pp. 431–432 (1990) and *Biotech Forum Europe*, Vol. 8, pp. 201–203 (1991), it was reported that the partially purified enzyme preparation obtainable from the cell and cell extract of *Sulfolobus solfataricus* (ATCC 49155) forms glucose and trehalose when allowed to act on substrate such as amylose and soluble starch. A purification of such an enzyme preparation can not be completed, however, as the physicochemical properties of the enzyme thus prepared are not sufficiently indicated and the action of the enzyme has not been clarified, and only a preparation of trehalose is indicated. Thus, there has been a great demand to establish a novel preparation of trehalose by utilizing a thermostable enzyme capable of acting at a temperature of over 55° C.

SUMMARY OF THE INVENTION

The present invention is to provide a novel preparation of trehalose to form trehalose or a saccharide composition containing the same. The trehalose is can be prepared from reducing partial starch hydrolysates by a thermostable trehalose-releasing enzyme which is capable of acting at a temperature of over 55° C. and clarifying its action, and to trehalose obtainable by said preparation and a saccharide composition containing the same as well as their uses.

In order to attain the aforementioned object, the present inventors, desiring an establishment of a novel thermostable enzyme which can release trehalose from non-reducing saccharides having a trehalose structure and having a degree of glucose polymerization of 3 or higher, have extensively screened microorganisms capable of producing said enzyme while centering around thermophilic microorganisms.

As a result, the present inventors found that microorganisms of the genus Sulfolobus, named as "*Sulfolobus acidocaldarius*" ATCC 33909 and ATCC 49426, and as "*Sulfolobus solfataricus*" ATCC 35091 and ATCC 35092, these as disclosed in Japanese Patent Application No. 166,011/94, produce a thermostable non-reducing saccharide-forming enzyme and also a novel thermostable trehalose-releasing enzyme which are capable of acting at a temperature of over 55° C., and found that the objective preparation of trehalose at a temperature of over 55° C. is readily conducted by allowing the thermostable non-reducing saccharide enzyme together with this novel thermostable trehalose-releasing enzyme to act on reducing partial starch hydrolysates. The present inventors also found that trehalose is readily preparable by allowing the thermostable non-reducing saccharide-forming enzyme together with the novel thermostable trehalose-releasing enzyme to act on reducing partial starch hydrolysates and subjecting to the action of glucoamylase or α-glucosidase to obtain reacted solutions containing trehalose with a relatively-high purity. Thus, the present inventors accomplished this invention.

BRIEF EXPLANATION OF THE ACCOMPANYING DRAWINGS

DETAILED DESCRIPTION OF THE INVENTION

Figure 1:
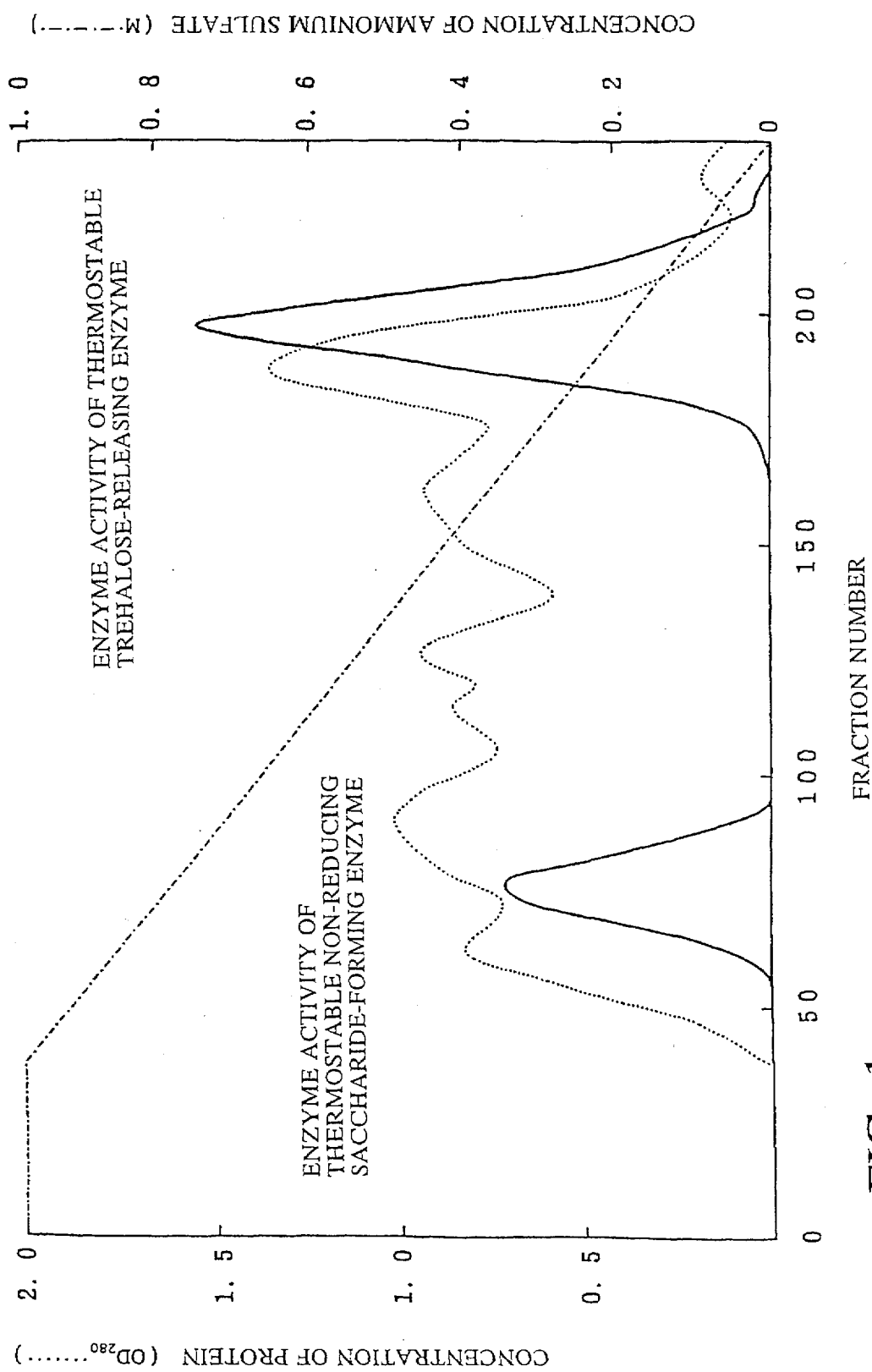
FIG. 1 shows elution patterns of the present thermostable trehalose-releasing enzyme and a non-reducing saccharide-forming enzyme eluted from a column packed with a gel of "DEAE-TOYOPEARL®".

The present invention relates to a novel thermostable trehalose-releasing enzyme, and its preparation and uses. The present invention further relates to a microorganism capable of producing said enzyme, trehalose prepared with said enzyme, and compositions containing the same.

The present inventors have extensively screened microorganisms capable of producing a novel thermostable trehalose-releasing enzyme which specifically hydrolyses the linkage between a trehalose moiety and the remaining glycosyl moiety in non-reducing saccharides having a trehalose structure and having a glucose polymerization degree of 3 or higher, and eventually found the objective microorganisms.

Now, the present inventors found that microorganisms of the genus Sulfolobus, named as "*Sulfolobus acidocaldarius*" ATCC 33909 and ATCC 49426, and as "*Sulfolobus solfataricus*" ATCC 35091 and ATCC 35092, are capable of producing a novel thermostable trehalose-releasing enzyme.

In addition to the above-mentioned microorganisms, other strains of the genus Sulfolobus and their mutants can be arbitrarily used in the present invention as long as they produce a thermostable trehalose-releasing enzyme which specifically hydrolyses the linkage between a trehalose moiety and the remaining glycosyl moiety in a non-reducing saccharide having a trehalose structure as an end unit and having a degree of glucose polymerization of 3 or higher.

Any nutrient culture medium can be used in the invention as long as these microorganisms can grow therein and produce the present thermostable trehalose-releasing enzyme: For example, synthetic- and natural-nutrient culture media can be used as the nutrient culture medium. Any carbon-containing substance can be used in the present invention as a carbon source as long as it is utilized by the microorganisms: Examples of such a carbon source are saccharides such as glucose, fructose, lactose, sucrose, mannitol, sorbitol, molasses and reducing partial starch hydrolysates; and organic acids such as citric acid, succinic acid and their salts. The concentrations of these carbon sources in nutrient culture media are appropriately chosen. For example, in the case of using reducing partial starch hydrolysates, a preferable concentration is usually 20% or lower, more particularly, 5% or lower, d.s.b., in view of the growth of microorganisms. The nitrogen sources usable in the present invention are, for example, inorganic nitrogen compounds such as ammonium salts and nitrates; and organic nitrogen-containing substances such as urea, corn steep liquor, casein, peptone, yeast extract and beef extract. The inorganic ingredients usable in the invention are, for example, calcium salts, magnesium salts, potassium salts, sodium salts, phosphates and other salts of manganese, zinc, iron, copper, molybdenum and cobalt.

The microorganisms usable in the present invention are cultured under aerobic conditions at a temperature, usually, in the range of 40°–95° C., preferably, in the range of 50°–90° C.; and at a pH in the range of 1–7, preferably, a pH in the range of 2–6. The cultivation time used in the present invention is set to a time required for the growth initiation of the microorganisms, preferably, 10–100 hours. The concentration of dissolved oxygen in nutrient culture media is not specifically restricted, but usually in the range of 0.5–20 ppm. For keeping the dissolved oxygen in nutrient culture media, the means of controlling of aeration, stirring, aeration with oxygen, and increasing the inner pressure of a fermenter can be utilized. The cultivation is carried out batchwise or in continuous manner.

After completion of the cultivation, the present enzyme is recovered from cultures. The activity of the present enzyme is found mainly in cells. It is preferable to purify these cells in the usual manner and to use the resultant as a crude enzyme preparation. For example, by dialyzing a crude enzyme preparation which had been prepared by salting out with an ammonium sulfate and concentrated, and successively purifying the dialyzed solution on anion-exchange column chromatography using "DEAE TOYOPEARL®", an anion-exchange resin, and further purifying by hydrophobic column chromatography using "BUTYL TOYOPEARL®", a hydrophobic resin; gel filtration chromatography using "TOYOPEARL® HW-55", a resin for gel filtration and hydrophobic column chromatography using "BUTYL TOYOPEARL®", a hydrophobic resin, all of which are products of Tosoh Corporation, Tokyo, Japan; gel filtration chromatography using "SUPER ROSE 12", a resin for gel filtration which a product of Pharmacis LKB, Uppsala, Sweden, a purified enzyme preparation exhibiting an electrophoretically single band can be prepared.

The present thermostable trehalose-releasing enzyme thus obtained has the following physicochemical properties:

(1) Action

Specifically hydrolysing the linkage between a trehalose moiety and the remaining glycosyl moiety in a non-reducing saccharide having a trehalose structure as an end unit and having a degree of glucose polymerization of 3 or higher;

(2) Molecular weight

About 54,000 to 64,000 daltons on sodium dodecylsulfate-polyacrylamide gel electrophoresis (SDS-PAGE);

(3) Isoelectric point (pI)

About 5.6 to 6.6 on isoelectrophoresis using ampholyte;

(4) Optimum temperature

About 75° C. when incubated at pH 6.0 for 30 min;

(5) Optimum pH

About 5.5 to 6.0 when incubated at 60° C. for 30 min;

(6) Thermal stability

Stable up to a temperature of about 85° C. when incubated at pH 7.0 for 60 min; and (7) pH stability Stable at a pH of about 4.5 to 9.5 when incubated at 25° C. for 16 hours.

The activity of the present thermostable trehalose-releasing enzyme is assayed as follows: One ml of an enzyme solution is added to 4 ml of 1.25 w/v % maltotriosyltrehalose ($\alpha$-maltotetraosyl $\alpha$-glucoside) in 50 mM phosphate buffer (pH 6.0) as a substrate, and the mixture solution is incubated at 60° C. for 30 min. The reaction solution is mixed with Somogyi copper liquor to suspend the enzymatic reaction, and followed by determining the reducing power of the solution on the Somogyi-Nelson's method. As a control, an enzyme solution, which had been heated at 100° C. for 30 min to inactivate any enzyme activity, is treated similarly as above. With such a determination, one unit activity of the present enzyme is defined as the amount of enzyme which increases the reducing power of that of one micromole of glucose per minute.

Non-reducing saccharides which can be used as a substrate for the present enzyme are those having a trehalose structure as an end unit and having a degree of glucose polymerization of 3 or higher. Examples of such a substrate are glucosyltrehalose, maltosyltrehalose, maltotriosyltrehalose, maltotetraosyltrehalose and maltopentaosyltrehalose which are obtainable by allowing a non-reducing saccharide-forming enzyme to act on maltotriose, maltotetraose, maltopentaose, maltohexaose and maltoheptaose. In addition, relatively-low reducing partial starch hydrolysates containing non-reducing saccharides which have a trehalose structure and a degree of glucose polymerization of 3 or higher, those prepared by allowing non-reducing saccharide-forming enzyme to act on reducing partial starch hydrolysates which are preparable by partially hydrolyzing amylaceous substances such as starch, amylopectin and amylose by amylases or acids, can be used.

As an amylase for hydrolyzing starch, for example, $\alpha$-amylase, maltopentaose-forming amylase, and maltohexaose-forming amylase as disclosed in *Handbook of Amylases and Related Enzymes*, published by Pergamon Press, Tokyo, Japan (1988), can be used. These amylases can be used favorably together with debranching enzymes such as pullulanase and isoamylase.

As non-reducing saccharide-forming enzymes which forms non-reducing saccharides having a trehalose structure and having a degree of glucose polymerization of 3 or higher when allowed to act on reducing partial starch hydrolysates, those derived from Rhizobium sp. M-11 or Arthrobactor sp. Q36 as disclosed in Japanese Patent Application No. 349, 216/93, can be used, however, in case that an enzymatic reaction proceeds at a temperature of over 55° C., the thermostable non-reducing saccharide-forming enzyme which belongs to the group of the genus Sulfolobus, disclosed in Japanese Patent Application No. 166,011/94, can be used favorably.

The concentration of substrates in the present invention is not specifically restricted. For example, in the case of using 0.1% or 50% solution of a substrate, the present enzymatic reaction proceeds to form a trehalose. Further a solution containing the excess amount of the substrate which is not dissolved completely can be used in the present invention. The reaction temperature used in the present enzymatic reaction can be set to a temperature at which the present enzyme is not inactivated, i.e. a temperature up to about 85° C., preferably, a temperature in the range of 55°–70° C. The reaction pH used in the present enzymatic reaction is controlled to in the range of 4–10, preferably, in the range of about 5–7. The reaction time used in the present enzymatic reaction is adequately chosen depending on the conditions of the enzymatic reaction.

A method of preparing a trehalose using reducing partial starch hydrolysates, according to the present invention, can prepare a remarkably increased amount of trehalose, in comparison with those disclosed in the specification of Japanese Patent Application No. 349,216/93, more particularly, contrasting with reaction solutions obtainable by the action of a non-reducing saccharide-forming enzyme together with glucoamylase. More particularly, the preparation percentage of trehalose obtainable by the action of a non-reducing saccharide-forming enzyme together with glucoamylase is about 30%, while that of trehalose obtainable by the reaction of a non-reducing saccharide-forming enzyme together with trehalose-releasing enzyme in the present invention is about 60% or higher.

The enzymatic reaction in the present invention is as follows: At first, one molecule of reducing partial starch hydrolysate having a degree of glucose polymerization of 3 or higher is converted into one molecule of non-reducing saccharide having a trehalose structure as an end unit by the action of non-reducing saccharide-forming enzyme, and further the resultant non-reducing saccharides are converted by the hydrolytic action of trehalose-releasing enzyme into one molecule of trehalose and one molecule of reducing partial starch hydrolysates of which a degree of glucose polymerization is decreased by 2. In case that reducing partial starch hydrolysates thus newly produced have a degree of glucose polymerization of 3 or higher, they are converted into non-reducing saccharides having a trehalose structure as an end unit by the action of non-reducing saccharide-forming enzyme, and followed by subjecting them to the action of trehalose-releasing enzyme to form one molecule of trehalose and reducing partial starch hydrolysates. By repeating these actions of non-reducing saccharide-forming enzyme and trehalose-releasing enzyme, several molecules of trehalose can be prepared from one molecule of reducing partial starch hydrolysates.

In the aforementioned enzymatic reaction, a non-reducing saccharide-forming enzyme and a trehalose-releasing enzyme of the present invention can be allowed to act simultaneously on reducing partial starch hydroylsates having a degree of glucose polymerization of 3 or higher, and at first a non-reducing saccharide-forming enzyme is allowed to act on said reducing partial starch hydroylsates, followed by subjecting to the action of trehalose-releasing enzyme of the present invention. If necessary, glycoamylase is allowed favorably to act on to increase the content of trehalose.

The resultant reaction mixtures are in the usual manner subjected to filtration and centrifugation to remove insoluble substances, and the resultant solutions are decolored with an activated charcoal, desalted with ion exchangers in H- and OH-form, and concentrated into syrupy products which can be dried into powdery products. If necessary, the powdery products can be readily prepared into non-reducing saccharides with the highest possible purity by purifying the powdery products. Examples of column chromatographic fractionations such as ion-exchange column chromatography, column chromatography using an activated charcoal or a silica gel; separations using organic acids such as alcohols and acetone; and alkaline treatments to decompose and remove the remaining reducing saccharides, and with these purifications, high-purity trehalose products are readily obtainable.

If necessary, the present non-reducing saccharides having a trehalose structure thus obtained can be hydrolyzed by amylases such as α-amylase, α-amylase, glucoamylase, α-glucosidase and trehalase, or subjected to a saccharide-transfer reaction by using cyclomaltodextrin glucanotransferase and/or glucosyltransferase to control their sweetness and reducing power as well as to reduce their viscosity. Furthermore, the saccharide products can be arbitrarily hydrogenated to convert them into sugar alcohols to eliminate their reducing power. From the resultant products glucose can be removed by using aforesaid purification methods such as ion-exchange column chromatography to prepare high trehalose content fractions. The fractions thus obtained can be arbitrarily purified and concentrated into syrupy products, and, if necessary the syrupy products can be further concentrated into supersaturated solutions and crystallized to obtain hydrous crystalline trehalose or anhydrous crystalline trehalose.

The ion-exchange column chromatographic techniques usable in the invention include, for example, those which use a strong-acid cation-exchange resin as disclosed in Japanese Patent Laid-Open Nos. 23,799/83 and 72,598/83. By using these techniques, concomitant saccharides contained in crude trehalose products can be readily removed to obtain high trehalose content products. In this case, any one of fixed-bed, moving bed and semi-moving methods can be arbitrarily employed.

To prepare hydrous crystalline trehalose, for example, an about 65–90% solution of trehalose with a purity of about 60% or higher, d.s.b., is placed in a crystallizer, if necessary, and gradually cooled while stirring in the presence of 0.1–20% seed crystal at a temperature of 95° C. or lower, preferably, at a temperature in the range of 10°–90° C., to obtain a massecuite containing hydrous crystalline trehalose. Also, the continuous crystallization to prepare hydrous crystalline trehalose while concentrating a solution of trehalose under reduced pressure can be favorably used in the present invention. Conventional methods such as separation, block pulverization, fluidized-bed granulation and spray drying can be employed in the present invention to prepare from the massecuite hydrous crystalline trehalose or crystalline saccharides containing the same.

In the case of separation, massecuites are usually subjected to a basket-type centrifuge to separate hydrous crystalline trehalose from the mother liquor, and, if necessary, the hydrous crystalline trehalose is washed by spraying thereto with a small amount of cold water to facilitate the preparation of hydrous crystalline trehalose with an increased purity. In the case of spray drying, crystalline saccharides with no or substantially no hygroscopicity are readily prepared by spraying massecuites with a concentration of 60–85%, d.s.b., and a crystallization percentage of about 20–60%, d.s.b., from a nozzle by a high-pressure pump; drying the resultant products with a 60°–100° C. hot air which does not melt the resultant crystalline powders; and aging the resultant powders for about 1–20 hours while blowing thereto 30°–60° C. hot air. In the case of block pulverization, crystalline saccharides with no or substantially no hygroscopicity are readily prepared by allowing massecuites with a moisture content of 10–20% and a crystallization percentage of about 10–60%, d.s.b., to stand for a period from about several hours to 3 days to crystallize and solidify the whole contents into blocks; and pulverizing or cutting the resultant blocks. Although anhydrous crystalline trehalose can be prepared by drying hydrous crystalline trehalose to convert it into anhydrous one, it is generally prepared by placing a high trehalose content solution with a moisture content less than 10% in a crystallizer; keeping the solution in the presence of a seed crystal at a temperature in the range of 50°–160° C., preferably, a temperature in the range of 80°–140° C. under stirring conditions to obtain a massecuite containing anhydrous crystalline trehalose; and crystallizing and pulverizing anhydrous crystalline trehalose at a relatively high temperature by conventional methods such as block pulverization, fluidized-bed granulation and spray drying.

The present trehalose thus obtained is stable and substantially free of reducing power, and can be mixed and processed with other materials, specifically, amino acids and amino acid-containing substances such as oligopeptides and proteins without fear of causing unsatisfactory browning and smell as well as deterioration of the materials. Trehalose per se has a satisfactorily-high quality and sweetness. Since trehalose is readily hydrolyzed by trehalase into glucose units, it is assimilated, absorbed and utilized by living bodies as a caloric source when orally administered. Furthermore, trehalose is not substantially fermented by dental carries-inducing microorganisms, and this renders it useful as a sweetener substantially free of inducing dental caries.

Trehalose can be utilized parenterally as a liquid feeding and infusion without fear of toxicity and side effects, preferably, utilized as an energy source by the body. Trehalose is a stable sweetener, and, especially crystalline trehalose is arbitrarily used as a sugar coating agent for tablets when used in combination with a binder such as pullulan, hydroxyethyl starch or polyvinylpyrrolidone. In addition, trehalose has properties such as osmotic pressure-controlling ability, filler-imparting ability, gloss-imparting ability, moisture-retaining ability, viscosity-imparting ability, ability to prevent crystallization of other saccharides, substantially no fermentability, and ability to prevent retrogradation of gelatinized starch.

Thus, the present trehalose and saccharide composition containing the same can be arbitrarily used as a sweetener, taste-improving agent, quality-improving agent, stabilizer and filler in a variety of compositions such as food products, cigarettes, tobaccos, feeds, cosmetics and pharmaceuticals.

The present trehalose and saccharide compositions containing the same can be used intact as a seasoning for sweetening. If necessary, they can be used together with adequate amounts of one or more other sweeteners, for example, powdered syrup, glucose, maltose, sucrose, isomerized sugar, honey, maple sugar, sorbitol, maltitol, lactitol, dihydrochalcone, stevioside, α-glycosyl stevioside, rebaudioside, glycyrrhizin, L-aspartyl L-phenylalanine methyl ester, saccharin, glycine and alanine; and/or a filler such as dextrin, starch and lactose.

The present trehalose and saccharide compositions containing the same in the form of a powder or a crystal can be used intact, or, if necessary they can be mixed with an excipient, diluent, filler and binder and formed into granules, spheres, shot-rods, plates, cubes and tablets, prior to their use. The present trehalose and saccharide compositions containing the same well harmonize with other materials having sourness, acidity, saltiness, bitterness, astringency and deliciousness-tastes, and have a relatively-high acid tolerance and heat resistance. Thus, they can be favorably used in food products in general as a sweetener, taste-improving agent and quality-improving agent.

The present trehalose and saccharide compositions containing the same can be used in seasonings such as soy sauce, powdered soy sauce, "miso", "funmatsu-miso" (a powdered miso), "moromi" (a refined sake), "hishio" (a refined soy sauce), "furikake" (a seasoned fish meal), mayonnaise, dressing, vinegar, "sanbai-zu" (a sauce of sugar, soy sauce and vinegar), "funmatsu-sushi-su" (powdered vinegar for sushi), "chuka-no-moto" (an instant mix for Chinese dish), "tentsuyu" (a sauce for Japanese deep-fat fried food), "mentsuyu" (a sauce for Japanese vermicelli), sauce, catsup, "yakiniku-no-tare" (a sauce for Japanese grilled meat), curry roux, instant stew mix, instant soup mix, "dashi-no-moto" (an instant stock mix), mixed seasoning, "mirin" (a sweet sake), "shin-mirin" (a synthetic mirin), table sugar and coffee sugar.

The present trehalose and saccharide compositions containing the same can be also used freely for sweetening "wagashi" (Japanese cakes) such as "senbei" (a rice cracker), "arare-mochi" (a rice-cake cube), "okoshi" (a millet-and-rice cake), "mochi" (a rice paste), "manju" (a bun with a bean-jam), "uiro" (a sweet rice jelly), "an" (a bean jam), "yokan" (a sweet jelly of beans), "mizu-yokan" (a soft adzuki-bean jelly), "kingyoku" (a kind of yokan), jelly, pao de Castella and "amedama" (a Japanese toffee); confectioneries such as bun, biscuit, cracker, cookie, pie, pudding, butter cream, custard cream, cream puff, waffle, sponge cake, doughnut, chocolate, chewing gum, caramel and candy; frozen desserts such as ice cream and sherbet; syrups such as "kajitsu-no-syrup-zuke" (a preserved fruit) and "korimitsu" (a sugar syrup for shaved ice); pastes such as flour paste, peanut paste, fruit paste and spread; processed fruits and vegetables such as jam, marmalade, "syrup-zuke" (fruit pickles) and "toka" (conserves); pickles and pickled products such as "fukujin-zuke" (red colored radish pickles), "bettara-zuke" (a kind of whole fresh radish pickles), "senmai-zuke" (a kind of sliced fresh radish pickles) and "rakkyo-zuke" (pickled shallots); premixes for pickles and pickled products such as "takuan-zuke-no-moto" (a premix for pickled radish) and "hakusai-zuke-no-moto" (a premix for fresh white rape pickles); meat products such as ham and sausage; products of fish meat such as fish ham, fish sausage, "kamaboko" (a steamed fish paste), "chikuwa" (a kind of fish paste) and "tempura" (a Japanese deep-fat fried fish paste); "chinmi" (relish) such as "uni-no-shiokara" (salted guts of sea urchin), "ika-no-shiokara" (salted guts of squid), "su-konbu" (processed tangle), "saki-surume" (dried squid strips) and "fugu-no-mirin-boshi" (a dried mirin-seasoned swellfish); "tsukudani" (foods boiled down in soy sauce) such as those of laver, edible wild plants, dried squid, fish and shellfish; daily dishes such as "nimame" (cooked beans), potato salad and "konbu-maki" (a tangle roll); milk products such as yoghurt and cheese; canned and bottled products such as those of meat, fish meat, fruit and vegetable; alcoholic beverages such as synthetic sake, wine and liquors; soft drinks such as coffee, tea, cocoa, juice, carbonated beverage, sour milk beverage and beverage containing a lactic acid bacterium; instant food products such as instant pudding mix, instant hot cake mix and "sokuseki-shiruco" (an instant mix of adzuki-bean soup with rice cake) and instant soup mix; and beverages such as baby foods, foods for therapy, and beverages supplemented with nutrition; as well as for improving the tastes and qualities of the aforementioned food-products.

The present trehalose and saccharide compositions containing the same can be also used in feeds and pet foods for animals such as domestic animals, poultry, honey bees, silk worms and fishes to improve their taste preferences. The trehalose and saccharide compositions containing the same can be arbitrarily used as a sweetener, taste-improving agent, quality-improving agent and stabilizer in other products in paste and liquid form such as a tobacco, cigarette, dentifrice, lipstick, rouge, lip cream, internal medicine, tablet, troche, cod liver oil in the form of a drop, cachou, oral refrigerant, gargle, cosmetic and pharmaceutical.

The present trehalose and saccharide compositions containing the same can be used as a quality-improving agent and stabilizer for biologically active substances susceptible to loss of their effective ingredients and activities, as well as in health foods and pharmaceutical compositions containing biologically active substances. Examples of such a biologically active substance are lymphokines such as $\alpha$-, $\beta$- and $\gamma$-interferons, tumor necrosis factor-$\alpha$ (TNF-$\alpha$), tumor necrosis factor-$\beta$ (TNF-$\beta$), macrophage migration inhibitory factor, colony-stimulating factor, transfer factor and interleukin 2 (IL-2); hormones such as insulin, growth hormone, prolactin, erythropoietin and follicle-stimulating hormone; biological preparations such as BCG vaccine, Japanese encephalitis vaccine, measles vaccine, live polio vaccine, smallpox vaccine, tetanus toxoid, Trimeresurus antitoxin and human immunoglobulin; antibiotics such as penicillin, erythromycin, chloramphenicol, tetracycline, streptomycin and kanamycin sulfate; vitamins such as thiamine, riboflavin, L-ascorbic acid, cod liver oil, carotenoid, ergosterol and tocopherol; enzymes such as lipase, elastase, urokinase, protease, $\beta$-amylase, isoamylase, glucanase and lactase; extracts such as ginseng extract, snapping turtle extract, chlorella extract, aloe extract and propolis extract; viable microorganisms such as viruses, lactic acid bacteria and yeasts; and other biologically active substances such as royal jelly. The present trehalose and saccharide compositions containing the same readily realize a preparation of the aforementioned biologically active substances into health foods and pharmaceutical compositions with a satisfactorily-high stability and quality without fear of losing or inactivating their effective ingredients and activities.

As described above, the methods to incorporate the present trehalose and saccharide compositions containing the same into the aforementioned substances and compositions include conventional methods, for example, mixing, kneading, dissolving, melting, soaking, permeating, sprinkling, applying, coating, spraying, injecting, crystallizing and solidifying. The trehalose and saccharide compositions containing the same are usually incorporated into the aforementioned substances and compositions in an amount of 0.1% or higher, preferably, one % or higher, d.s.b.

The following experiments explain the present invention in more detail:

Experiment 1

Production of enzyme

A liquid nutrient culture medium, consisting of 0.1 w/v % peptone, 0.1 w/v % yeasts extract, 0.2 w/v % ammonium sulfate, 0.05 w/v % potassium phosphate, 0.02 w/v % magnesium sulfate, 0.02 w/v % potassium chloride and

11 water, was prepared. About 100 ml aliquots of the nutrient culture medium were placed in 500-ml Erlenmeyer flasks, autoclaved at 120° C. for 20 minutes to effect sterilization, cooled and adjusted to pH 3.0 by the addition of sulphate, and then inoculated with a stock culture of *Sulfolobus acidocaldarius* ATCC 33909 and incubated at 75° C. for 24 hours under stirring conditions of 130 rpm. The resultant cultures were pooled and used as a first seed culture. About 5 liter of a fresh preparation of the same nutrient culture medium as that used in the first seed culture was placed in a 10-liter fermenter, sterilized, cooled to 75° C. and adjusted to pH 3.0, and then inoculated with one v/v % of the first seed culture and incubated at 75° C. for about 48 hours while stirring under aerobic conditions at an aeration of 500 ml/min to obtain a second seed culture. About 250 liter of a fresh preparation of the same nutrient culture medium as that used in the first seed culture was placed in a 300-liter fermenter, sterilized, cooled to 75° C. and adjusted to pH 3.0, and then inoculated with one v/v % of the second seed culture and incubated at 75° C. for about 42 hours while stirring under aerobic conditions at an aeration of 100 ml/min. The present trehalose-releasing enzyme accumulated in the culture were respectively about 0.03 units/ml.

Experiment 2

Purification of enzyme

About 170 liters of the culture obtained by the method in Experiment 1 was centrifuged to recover about 258 g wet cells. The cells thus recovered were suspended in 300 ml of 10 mM phosphate buffer (pH 7.0) and treated with "US 300", a ultrasonic cell disrupting apparatus commercialized by Nippon Seiki, Co., Ltd., Niigate, Japan, to disrupt cells. The resultant mixture was centrifuged at 10,000 rpm for 30 minutes to obtain an about 300 ml supernatant. To the supernatant was added ammonium sulfate and dissolved to give a saturation degree of 0.7, and the resultant solution was allowed to stand at 4° C. for 24 hours, and centrifuged to obtain a precipitate. The resultant precipitate was dissolved in 10 mM Tris-HCl buffer (pH 8.5), and dialyzed against a fresh preparation of the same buffer for 24 hours, and centrifuged to remove insoluble substances. The resultant dialyzed solution (about 600 ml) was divided into 2 portions which were then separately subjected to column chromatography using a column packed with about 350 ml of "DEAE-TOYOPEARL®", an ion exchanger commercialized by Tosoh Corporation, Tokyo, Japan.

The objective thermostable trehalose-releasing enzyme and thermostable non-reducing saccharide-forming enzyme adsorbed on "DEAE-TOYOPEARL®" were eluted from the column with 10 mM Tris-HCl buffer containing 0.1M sodium chloride. The resultant fractions were recovered.

The fractions thus obtained were dialyzed against a fresh preparation of 10 mM Tris-HCl buffer containing 1M ammonium sulfate. The dialyzed solutions thus obtained were centrifuged to remove insoluble substances, and the resultant supernatants were subjected to hydrophobic column chromatography using a column packed with 350 ml of "BUTYL-TOYOPEARL® 650", a hydrophobic gel commercialized by Tosoh Corporation, Tokyo, Japan. When material adsorbed on the gel was eluted from the column with a linear gradient buffer containing 1M to 0M ammonium sulfate, the thermostable trehalose-releasing enzyme and thermostable non-reducing saccharide-forming enzyme were eluted at different ammonium sulfate concentrations. The elution pattern of the column packed with "BUTYL-TOYOPEARL® was as shown in FIG. 1. The thermostable

12 non-reducing saccharide-forming enzyme was eluted from the column at an ammonium sulfate concentration of about 0.2M, while the trehalose-releasing enzyme was eluted from the column at an ammonium sulfate concentration of about 0.2M. The fractions containing either of the objective enzymes were separately pooled and purified.

The enzyme preparation of thermostable non-reducing saccharide-forming enzyme was dialyzed against a fresh preparation of 10 mM Tris-HCl buffer containing 0.2M sodium chloride, and the dialyzed solution was centrifuged to remove insoluble substances. The resultant supernatant was subjected to gel filtration chromatography using "ULTROGEL AcA 44®", a resin for gel filtration commercialized by Sepracor Inc., Marlborough, Mass. 01752, U.S.A., to recover fractions with the enzyme activity. The resultant fractions were dialyzed against a fresh preparation of 10 mM Tris-HCl buffer, and the resultant supernatant was subjected to column chromatography using a column packed with 10 ml of "MONO Q®", an ion exchanger commercialized by Pharmacia LKB, Uppsala, Sweden. The enzyme adsorbed on the ion exchanger was eluted from the column with a linear gradient buffer ranging from 0.2M to 0M sodium chloride, followed by recovering the fractions eluted from the column at about 0.1M sodium chloride.

The objective thermostable trehalose-releasing enzyme was purified by subjecting the fractions eluted from a column packed with "BUTYL-TOYOPEARL®" to gel filtration chromatography using "TOYOPEARL® HW-55" to recover fractions with the enzyme activity. The resultant fractions were subjected again to hydrophobic column chromatography using a column packed with "BUTYL-TOYOPEARL® 650", followed by subjecting to gel filtration chromatography using "SEPER ROSE 12HR 10/30" to recover fractions with the enzyme activity of the thermostable trehalose-releasing enzyme.

In the specification, unless specified otherwise, the activity of the present thermostable non-reducing saccharide-forming enzyme is designated the unit activity assayed as follows: One ml of an enzyme solution is added to 4 ml of 1.25 w/v % maltopentaose in 50 mM phosphate buffer (pH 5.5) as a substrate, and the mixture solution is incubated at 60° C. for 60 min. The reaction mixture is heated at 100° C. for 100 min to suspend the enzymatic reaction, and the reaction mixture is precisely diluted by 10 times with deionized water, followed by determining the reducing power of the diluted solution on the Somogyi-Nelson's method. One unit activity of said enzyme is defined as the amount of enzyme which diminishes under the above conditions the reducing power of that of one micromole of maltopentaose per minute.

The enzyme activity, specific activity and yield of the thermostable non-reducing saccharide-forming enzyme in each purification step are as shown in Table 1, while those of the present thermostable trehalose-releasing enzyme are as shown in Table 2.

TABLE 1

| Purification step | Total enzyme activity (units) | Specific activity (units/ mg protein) | Yield (%) |
| --- | --- | --- | --- |
| Material culture | ND | ND | ND |
| Supernatant after cell disruption | ND | ND | ND |
| Dialyzed solution | ND | ND | ND |

TABLE 1-continued

| Purification step | Total enzyme activity (units) | Specific activity (units/ mg protein) | Yield (%) |
|---|---|---|---|
| after salting out | | | |
| Eluate from ion-exchange column | ND | ND | ND |
| Eluate from hydrophobic column | 440 | 19.8 | 100 |
| Eluate after gel filtration column | 152 | 54.7 | 35 |
| Eluate from ion-exchange column | 39.8 | 80.8 | 9.0 |

Note: The "ND" in this Table means "not determining".

TABLE 2

| Purification step | Total enzyme activity (units) | Specific activity (units/ mg protein) | Yield (%) |
|---|---|---|---|
| Material culture | 4,550 | — | 100 |
| Supernatant after cell disruption | 4,450 | 0.22 | 98 |
| Dialyzed solution after salting out | 4,340 | 0.23 | 95 |
| Eluate from ion-exchange column | 3,290 | 1.35 | 72 |
| Eluate from hydrophobic column | 2,470 | 36.5 | 54 |
| Eluate from gel filtration column | 2,020 | 54.7 | 44 |
| Eluate from hydrophobic column | 820 | 128 | 18 |
| Eluate from gel filtration column | 147 | 730 | 3.2 |

The purified enzyme preparations, obtained as an eluate from gel filtration column in Tables 1 and 2, were examined their purity on electrophoresis using 7.5% polyacrylamide gel. As a result, each enzyme preparation observed in a single protein band meaning a highly purified preparation.

Experiment 3

Physicochemical properties

Experiment 3-1

Properties of thermostable trehalose-releasing enzyme

A portion of a purified thermostable trehalose-releasing enzyme preparation, obtained by the method in Experiment 2, was subjected to electrophoresis using a gel containing 10% sodium dodecylsulfate polyacrylamide, and determined its molecular weight to be about 54,000–64,000 daltons by making a comparison with marker proteins commercialized by Japan Bio-Rad Laboratories, Tokyo, Japan.

Another portion of the purified enzyme preparation was subjected to isoelectrophoresis using polyacrylamide gel containing 2 v/v % "AMPHOLINE", an ampholyte commercialized by Pharmacia LKB Biotechnology AB, Uppsala, Sweden. The resultant gel was sliced into pieces, followed by measuring their pHs and resulting in a pI of the enzyme being about 5.6–6.6.

Figure 2:
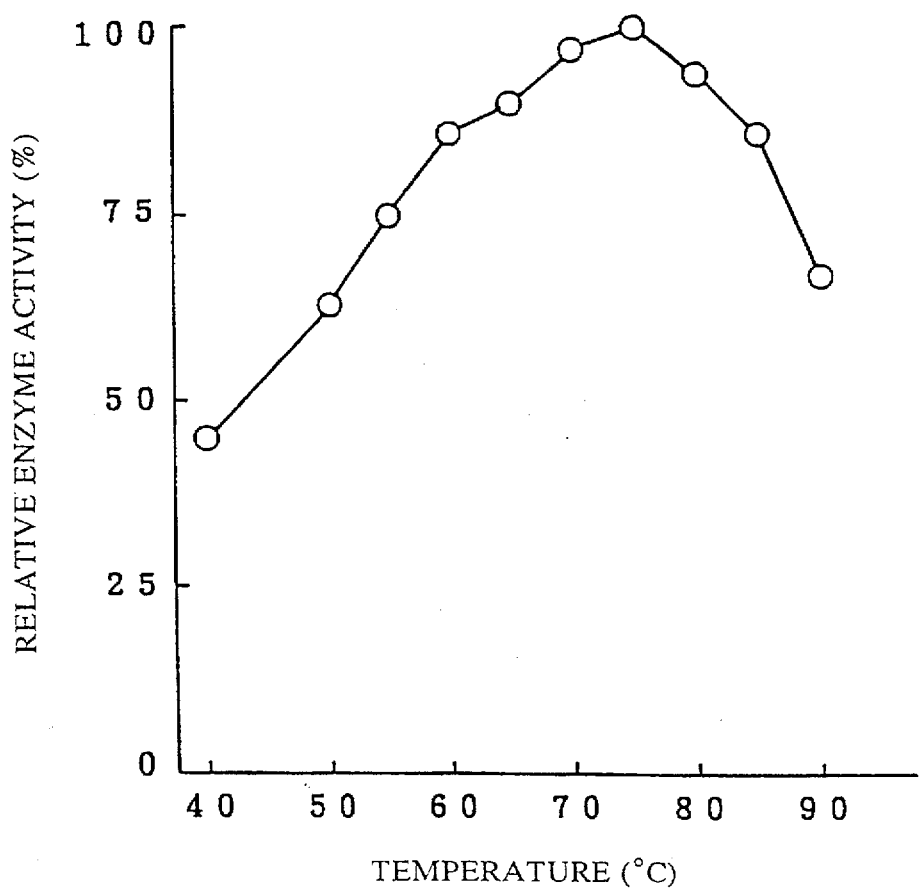
FIG. 2 shows the influence of temperature on the activity of the present thermostable trehalose-releasing enzyme.
Figure 3:
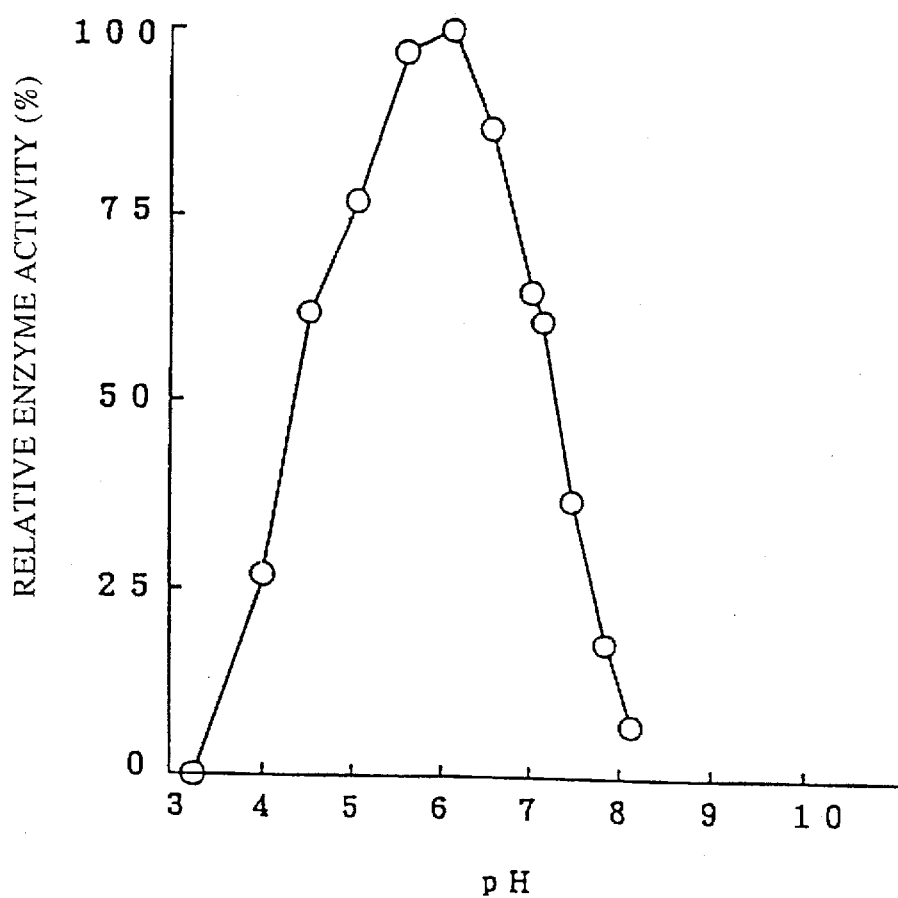
FIG. 3 shows the influence of pH on the activity of the present thermostable trehalose-releasing enzyme.
Figure 4:
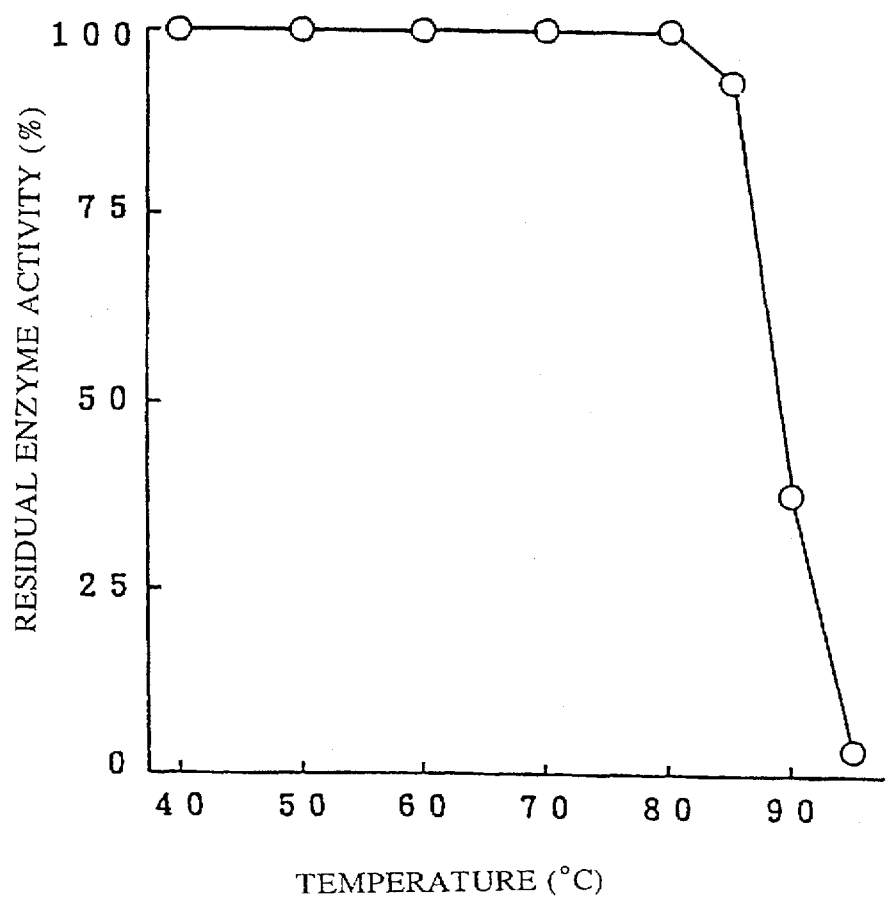
FIG. 4 shows the influence of temperature on the stability of the present thermostable trehalose-releasing enzyme.
Figure 5:
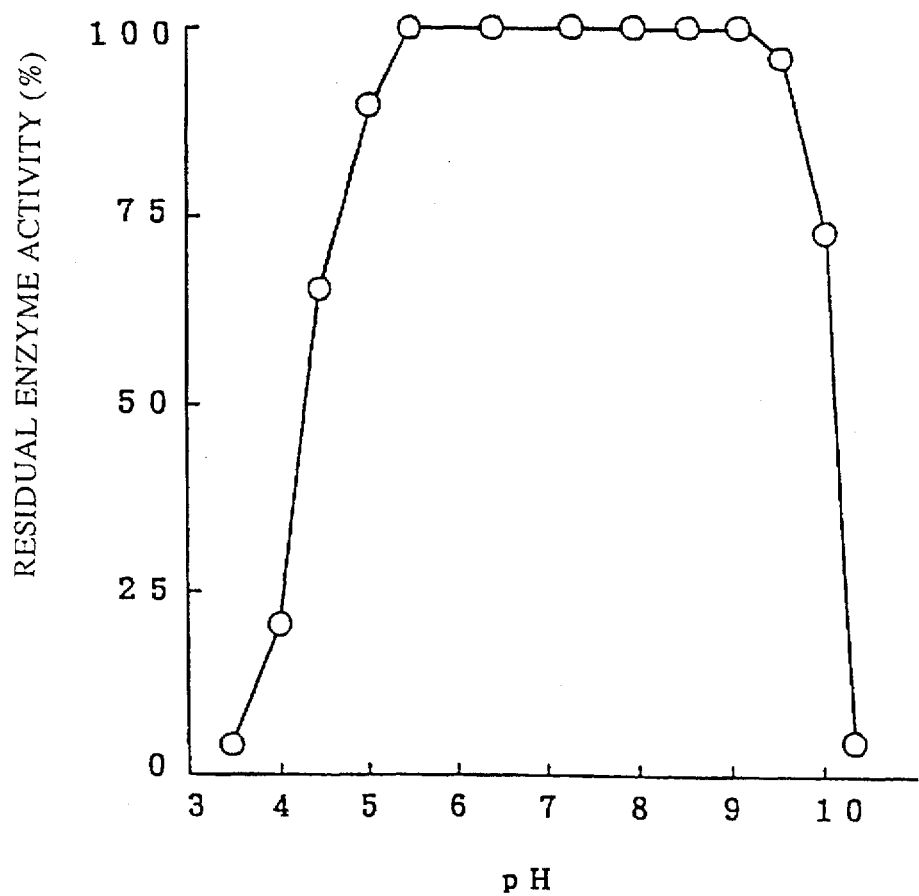
FIG. 5 shows the influence of pH on the stability of the present thermostable trehalose-releasing enzyme.

Effects of temperature and pH on the enzyme according to the present invention were studied in accordance with the assay as used for the enzyme activity. These results were respectively shown in FIG. 2 (effect of temperature) and FIG. 3 (effect of pH). The optimum temperature of the enzyme was about 75° C. when incubated at pH 6.0 for 30 min and the optimum pH was about 5.5–6.0 when incubated at 60° C. for 30 min. The thermal stability of the enzyme was determined by incubating it in 50 mM phosphate buffers (pH 7.0) for 60 min at different temperatures, cooling the buffers with cold water, and determining the remaining enzyme activity in each buffer. The pH stability of the enzyme was determined by incubating it in 50 mM phosphate buffers having different pHs at 25° C. for 16 hours, adjusting the buffers to pH 7, and assaying the remaining enzyme activity in each buffer. The results of the thermal stability and pH stability of the enzyme were respectively shown in FIGS. 4 and 5. The enzyme was stable up to a temperature of about 85° C. and at a pH of about 5.5–9.5.

The amino acid sequence of the present enzyme was analyzed on "MODEL 473A", a protein sequencer, commercialized by Perkin-Elmer Corp., Instrument Div., Norwalk, U.S.A., to reveal the 10 amino acid residues from the N-terminal. The partial amino acid sequence containing the N-terminal was methionine-phenylalanine-serine-phenylalanine-glycine-glycine-asparagine-isoleucine-glutamine-lysine (SEQ. ID. NO: 1).

Experiment 3-2

Properties of thermostable non-reducing saccharides-forming enzyme

The purified thermostable non-reducing saccharide-forming enzyme, obtained by the method in Experiment 2, was determined for molecular weight on SDS-polyacrylamide gel electrophoresis (10% gel concentration) by comparing with molecular weight of the marker electrophoresed simultaneously so as to exhibit an electrophoretically single band corresponding to about 69,000–79,000 daltons. The present purified enzyme was isoelectrophoresed in a polyacrylamide gel, and the pH of the resultant gel was adjusted to and the pI of the enzyme was determined to give a pI of about 5.4–6.4.

Effects of temperature and pH on the activity of the present enzyme were studied in accordance with the assay as used for the enzyme activity. The present enzyme gave an optimum temperature of about 75° C. and an optimum pH of 5.0–5.5. The thermal stability and pH stability of the present enzyme were studied in accordance with the method in Experiment 3–1. The present enzyme was stable up to a temperature of about 85° C. and at a pH of about 4.0–9.5.

The amino acid sequence of the present enzyme was analyzed in accordance with the method in Experiment 3–1. The partial amino acid sequence containing the N-terminal was methionine-isoleucine-serine-alanine-threonine-tyrosine-arginine-leucine-glutamine-leucine (SEQ. ID. NO: 2).

Experiment 4

Production of trehalose by thermostable trehalose-releasing enzyme

Experiment 4-1

Preparation of non-reducing saccharide-forming enzyme

A liquid nutrient culture medium, consisting of 2.0 w/v % maltose, 0.5 w/v % peptone, 0.1 w/v % yeasts extract, 0.1 w/v % disodium hydrogenphosphate and 0.1 w/v % dipotassium hydrogenphosphate, was prepared. About 100 ml aliquots of the nutrient culture medium were placed in 500-ml Erlenmeyer flasks, autoclaved at 120° C. for 20 minutes to effect sterilization, cooled, inoculated with a stock culture of Rhizobium sp. M-11 (FERM BP-4130), and incubated at 27° C. for 24 hours under shaking conditions. The resultant cultures were pooled and used as a seed culture. Separately, 20 liters of a fresh preparation of the same nutrient culture medium used in the above culture was placed in a 30-liter fermenter, sterilized, inoculated with one v/v % of the seed culture, and incubated at 30° C. for about 72 hours while keeping the pH of the culture at 6–8 and stirring under aerobic conditions with aeration. The resultant culture was treated with "MINI-LAB", a superhigh-pressure cell homogenizer, commercialized by Dainippon Pharmaceutical Co., Osaka, Japan to crush cells. The resultant was centrifuged to remove insoluble substances, followed by salting out with ammonium sulfate and successively purifying with ion-exchange column chromatography using "DEAE TOYOPEARL®", an anion-exchange resin; hydrophobic column chromatography using "BUTYL TOYOPEARL®", a hydrophobic resin; gel filtration chromatography using "TOYOPEARL® HW-55", a resin for gel filtration, all of which are products of Tosoh Corporation, Tokyo, Japan, to recover the non-reducing saccharide-forming enzyme preparation having specific activity of 195 units/mg protein at the yield of about 220 units which was calculated in term of one unit/liter of the culture.

The activity of the non-reducing saccharide-forming enzyme derived from Rhizobium sp. M-11 was assayed in accordance with the methods in Experiment 2 wherein 50 mM phosphate buffer (pH 7.0) used as a substrate and a reaction temperature of 60° C. were replaced by 50 mM acetic acid buffer (pH 5.5) and 40° C. respectively.

Experiment 4-2

Preparation of non-reducing saccharide having a trehalose structure as an end unit and having a degree of glucose polymerization of 3 or higher To an aqueous solution containing 20% maltotriose, maltotetraose, maltopentaose, maltohexaose or maltoheptaose as a substrate was added 2 units/g substrate, d.s.b., of a purified enzyme preparation obtained by the method in Experiment 4-1, and the resultant mixture was subjected to an enzymatic reaction at 40° C. and pH 7.0 for 48 hours. The reaction mixture was heated to inactivate the remaining enzyme, filtered, decolored, desalted and concentrated to obtain a concentrated saccharide solution which was then subjected to ion-exchange column chromatography using "XT-1016 (Na$^+$-form, polymerization degree of 4%)", an ion-exchanger commercialized by Tokyo Organic Chemical Industries, Ltd., Tokyo, Japan. In the column chromatography, the ion-exchanger was packed in 3-jacketed stainless-steel columns, having an inner diameter of 2.0 cm and a length of one m, which were then cascaded in series, heated to give the inner column temperature of 55° C., applied with 5 v/v % of the concentrated saccharide solution against the resin while maintaining the temperature at 55° C., and fed with 55° C. hot water at SV (space velocity) of 0.13 to obtain the fractions of high-purity non-reducing saccharides having a trehalose structure as an end unit and having a degree of polymerization of 3 or higher. Among the resultant fractions, the purity of non-reducing saccharides in its high-purity preparation was 95.0% or higher, d.s.b. The fractions thus obtained were collected and the solution was dissolved in 0.1N sodium hydroxide, and heated at 100° C. for 2 hours to decompose the remaining reducing saccharides. The resultant solution was decolored with activated charcoal and purified with ion-exchanger (H$^+$ and OH$^-$ form) to obtain the preparations rich in non-reducing saccharide preparations, and the purities of α-glucosyltrehalose, α-maltosyltrehalose, α-maltotriosyltrehalose, α-maltotetraosyltrehalose and α-maltopentaosyltrehalose in their high-purity preparations were respectively 99.0% or higher, d.s.b.

Experiment 4-3

Preparation of trehalose from non-reducing saccharides by thermostable trehalose-releasing enzyme An aqueous solution containing 5%, d.s.b., of each one of the above five non-reducing saccharide preparations obtained by the method in Experiment 4-2, was mixed with 2 units/g substrate, d.s.b., of the purified trehalose-releasing enzyme obtained in Experiment 2, and subjected to an enzymatic reaction at 60° C. and pH 5.5 for 48 hours. Each resultant reaction mixture was desalted and analyzed its composition on high-performance liquid chromatography (HPLC) using "WAKOBEADS WB-T-330", a column of Wako Pure Chemical Industries Ltd., Tokyo, Japan. As a control, a fresh preparation of the same enzyme was allowed to act on maltooligosaccharides such as maltotriose, maltotetraose, maltopentaose, maltohexaose and maltoheptaose. The resultant reaction mixture was analyzed its composition on HPLC. The results were in Table 3.

The results in Table 3 evidently show that:

1. Thermostable trehalose-releasing enzyme of the present invention specifically hydrolyzes the linkage between a trehalose moiety and a glycosyl moiety in a non-reducing saccharide having a trehalose structure as an end unit and a degree of glucose polymerization of 3 or higher to form trehalose and a non-reducing saccharide having a degree of glucose polymerization of one or more; and 2. Maltooligosaccharides are not hydrolyzed by the present trehalose-releasing enzyme.

TABLE 3

| Substrate | Product | Elution time on HPLC (min) | Percentage (%) |
| --- | --- | --- | --- |
| Glucosyltrehalose | Trehalose | 27.4 | 7.2 |
| | Glucose | 33.8 | 3.9 |
| | Glucosyltrehalose | 23.3 | 88.9 |
| Maltosyltrehalose | Trehalose | 27.4 | 40.2 |
| | Maltose | 28.7 | 40.5 |
| | Maltosyltrehalose | 21.6 | 19.3 |
| Maltotriosyltrehalose | Trehalose | 27.4 | 41.1 |
| | Maltotriose | 25.9 | 58.2 |
| | Maltotriosyltrehalose | 19.7 | 0.7 |
| Maltotetraosyltrehalose | Trehalose | 27.4 | 34.0 |
| | Maltotetraose | 24.1 | 65.8 |
| | Maltotetraosyltrehalose | 18.7 | 0.2 |
| Maltopentaosyltrehalose | Trehalose | 27.4 | 29.1 |
| | Maltotetraose | 22.6 | 70.6 |
| | Maltotetraosyltrehalose | 17.8 | 0.3 |
| Maltotriose | Maltotriose | 25.9 | 100 |
| Maltotetraose | Maltotetraose | 24.1 | 100 |
| Maltopentaose | Maltopentaose | 22.6 | 100 |
| Maltohexaose | Maltohexaose | 21.8 | 100 |
| Maltoheptaose | Maltoheptaose | 21.0 | 100 |

From these results, it is confirmed that the thermostable trehalose-releasing enzyme according to the present invention is a novel enzyme which has a mechanism of specifically hydrolyzing the linkage between a trehalose moiety and the remaining glycosyl moiety in a non-reducing saccharide having a trehalose structure as an end unit and having a degree of glucose polymerization of 3 or higher to release trehalose from the non-reducing saccharide.

Experiment 5

Preparation of trehalose from non-reducing partial starch hydrolysates

A suspension containing 5% waxy corn starch was gelatinized by heating, adjusted to pH 4.5, heated to 50° C., mixed with 4,000 units/g starch, d.s.b., of an isoamylase specimen commercialized by Hayashibara Biochemical Laboratories Inc., Okayama, Japan, and subjected to an enzymatic reaction for 20 hours. The reaction mixture was autoclaved at 120° C. for 10 min, cooled to 60° C., and subjected to gel filtration column chromatography using a column packed with 750 ml of "Toyopearl® HW", commercialized by Tosoh Corporation, Tokyo, Japan, to obtain reducing partial starch hydrolysates having a degree of glucose polymerization of 37-11.

The reducing partial starch hydrolysates thus obtained or maltotriose having a degree of glucose polymerization of 3 as a substrate was dissolved in 10 mM phosphate buffer (pH 7.0) into a one % solution which was then mixed with 4 units/g substrate, d.s.b., of a purified non-reducing saccharide-forming enzyme and a purified trehalose-releasing enzyme prepared by the method in Experiment 2, and subjected to an enzymatic reaction at 40° C. for 24 hours. After completion of the enzymatic reaction, a portion of resultant reaction mixture was desalted and analyzed on HPLC to identify its composition. Each remaining each reaction mixture was heated to 50° C., adjusted to pH 4.5, admixed with 50 units/g substrate, d.s.b., of a glucoamylase specimen commercialized by Seikagaku-Kogyo Co., Ltd., Tokyo, Japan, and subjected to an enzymatic reaction for 10 hours. Similarly as above, a portion of each resultant reaction mixture was desalted and analyzed on HPLC to analyze its composition. The results were as shown in Table 4.

As is shown in Table 4, in the case of using as a substrate maltotriose having a degree of glucose polymerization of 3, the trehalose yield after enzymatic reaction using a thermostable non-reducing saccharide-forming enzyme and the present thermostable trehalose-releasing enzyme was relatively low, i.e. 2.2%, while in the case of using as a substrate partial starch hydrolysates having a degree of glucose polymerization of 10.8-36.8, the trehalose yield was relatively high, i.e. 63.3-81.2%. It was found that the higher the degree of glucose polymerization of reducing partial starch hydrolysates as a material, the higher the purity of the resultant trehalose. It was also found that the purity of the resultant trehalose can be more increased by allowing glucoamylase to act on the reaction mixture prepared by the above two enzymes, to decompose the concomitant non-reducing saccharides, having a trehalose structure as an end unit and
having a degree of glucose polymerization of 3 or higher, into trehalose and glucose molecules.

TABLE 4

| Degree of glucose polymerization of reducing partial starch hydrolysate | Reaction product | Composition (%) | |
|---|---|---|---|
| | | A* | B** |
| 36.8 | Trehalose | 81.2 | 82.5 |
| | Glucose | 1.2 | 17.5 |

TABLE 4-continued

| Degree of glucose polymerization of reducing partial starch hydrolysate | Reaction product | Composition (%) | |
|---|---|---|---|
| | | A* | B** |
| | Reducing oligosaccharides | 13.6 | 0.0 |
| | α-glycosyltrehalose | 4.0 | 0.0 |
| 27.5 | Trehalose | 79.5 | 81.8 |
| | Glucose | 1.8 | 18.2 |
| | Reducing oligosaccharides | 14.1 | 0.0 |
| | α-glycosyltrehalose | 4.6 | 0.0 |
| 19.8 | Trehalose | 77.3 | 80.2 |
| | Glucose | 2.2 | 19.8 |
| | Reducing oligosaccharides | 15.3 | 0.0 |
| | α-glycosyltrehalose | 5.2 | 0.0 |
| 16.5 | Trehalose | 73.4 | 77.5 |
| | Glucose | 2.5 | 22.5 |
| | Reducing oligosaccharides | 18.1 | 0.0 |
| | α-glycosyltrehalose | 6.0 | 0.0 |
| 10.8 | Trehalose | 63.3 | 68.5 |
| | Glucose | 5.7 | 31.5 |
| | Reducing oligosaccharides | 22.8 | 0.0 |
| | α-glycosyltrehalose | 8.2 | 0.0 |
| 3 (Maltotriose) | Trehalose | 2.2 | 19.9 |
| | Glucose | 10.4 | 80.1 |
| | Maltose | 18.5 | 0.0 |
| | Maltotriose | 42.0 | 0.0 |
| | α-glucosyltrehalose | 26.9 | 0.0 |

Note:
The symbol "*" means a composition after enzymatic reaction of a non-reducing saccharide-forming enzyme and the present trehalose-releasing enzyme, and the symbol "**" means a composition after enzymatic reaction of glucoamylase. In the Table, the wording "α-glycosyltrehalose" means non-reducing saccharides having a trehalose structure as an end unit and having a degree of glucose polymerization degree of 3 or higher.

Experiment 6

Preparation of thermostable trehalose-releasing enzyme from other microorganisms of the genus Sulfolobus and its properties A nutrient culture medium was prepared, inoculated with microorganisms, and incubated for 42 hours in a fermenter by the same method in Experiment 1 except that *Sulfolobus acidocaldarius* (ATCC 49426), *Sulfolobus solfataricus* (ATCC 35091) and *Sulfolobus solfataricus* (ATCC 35092) were used as microorganisms in place of *Sulfolobus acidocaldarius* (ATCC 33909). According to the methods in Experiment 2, the cells were recovered from about 170 L of each resultant culture, disrupted with ultrasonic to obtain a supernatant. The resultant supernatant was salted out with ammonium sulfate, dialyzed, subjected to an ion-exchange column and hydrophobic column chromatography to obtain a partially purified enzyme preparation, and followed by studying its properties. The results were in Table 5 together with those obtained in the case of using *Sulfolobus acidocaldarius* (ATCC 33909).

According to the method in Experiment 4–3, trehalose was prepared by using these partially purified enzyme preparations, and studied on its structure to find that, similarly as the thermostable trehalose-releasing enzyme from *Sulfolobus acidocaldarius* (ATCC 33909), every enzyme preparation released trehalose from non-reducing saccharides having a trehalose structure as an end unit and a degree of glucose polymerization of 3 or higher.

TABLE 5

| Microorganism | Enzyme activity in eluate from ion-exchange column (unit) | Optimum temperature (°C.) | Optimum pH | Thermal stability (°C.) | pH stability |
| --- | --- | --- | --- | --- | --- |
| Sulfolobus acidocaldarius (ATCC 33909) | 2470 | About 75° C. | About 5.5–6.0 | Up to about 85° C. | About 5.5–9.5 |
| Sulfolobus acidocaldarius (ATCC 49426) | 1850 | About 75° C. | About 5.5–6.0 | Up to about 85° C. | About 5.5–9.5 |
| Sulfolobus solfatarius (ATCC 35091) | 1220 | About 75° C. | About 5.5–6.0 | Up to about 85° C. | About 4.5–8.5 |
| Sulfolobus solfatarius (ATCC 35092) | 445 | About 75° C. | About 5.5–6.0 | Up to about 85° C. | About 4.5–8.5 |

The following Examples A illustrate the preparation of the present thermostable trehalose-releasing enzyme, trehalose by using said enzyme, and saccharides containing the same; and Examples B illustrate compositions incorporating trehalose and saccharides containing the same.

EXAMPLE A-1

A seed culture of *Sulfolobus acidocaldarius* (ATCC 33909) was incubated by a fermenter for about 42 hours in accordance with the method in Experiment 1. After completion of the incubation, the resultant culture was concentrated with an SF-membrane to obtain about 5 L of cell suspension. The resultant suspension was treated with "MINI-LAB", a superhigh-pressure cell homogenizer, commercialized by Dainippon Pharmaceutical Co., to disrupt the cells. The resultant solution was centrifuged to recover about 4.8 L of supernatant. To the resultant supernatant was added ammonium sulfate to give a supersaturation degree of about 0.7, and the resultant solution was salted out and centrifuged to obtain a precipitate. The precipitate was dissolved in 10 mM tris-hydrochloride acid buffer (pH 8.5), and dialyzed against a fresh preparation of the same hydrochloride acid buffer. The resultant dialyzed solution was subjected five times to an ion-exchange column chromatography using a column packed with about 2 L of "SEPABEADS FP-DA13" which was equilibrated with said hydrochloride acid buffer, a gel commercialized by Mitsubishi Chemical Industries Ltd., Tokyo, Japan. The objective enzyme adsorbed on the ion exchanger was eluted from the column with a linear gradient buffer supplemented 0M to 0.5M sodium chloride, followed by recovering fractions with enzyme activity which was eluted from the column at about 0.15M sodium chloride. The resultant fractions were concentrated with an SF-membrane, and followed by recovering about 300 ml concentrated enzyme solution containing 32.6 units/ml of thermostable non-reducing saccharide-forming enzyme and 58.5 units/ml of thermostable trehalose-releasing enzyme. The fractions with enzyme activity thus recovered were dialyzed against a fresh preparation of 10 mM Tris-HCl buffer containing 1M ammonium sulfate, and the dialyzed solution thus obtained was centrifuged to remove insoluble substances. The resultant supernatant was subjected five time to hydrophobic column chromatography using a column packed with 350 ml of "BUTYL-TOYOPEARL® 650", a hydrophobic gel commercialized by Tosoh Corporation, Tokyo, Japan, and followed by separating thermostable non-reducing saccharide-forming enzyme and thermostable trehalose-releasing enzyme. To the suspension of potato starch having a concentration of 15 w/v % was added calcium carbonate to give a final concentration of 0.1 w/w %, adjusted to pH 6.0, admixed with "TERMAMYL 60L", α-amylase commercialized by Novo Industri A/S, Copenhagen, Denmark, to give a concentration of 0.2 w/w % per g starch and subjected to an enzymatic reaction at 95° C. for 15 min. The resultant mixture was autoclaved for 30 min (2 kg/cm$^2$), cooled to 58° C., adjusted to pH 5.5, admixed with 2,000 units/g starch of isoamylase commercialized by Hayashibara Biochemical Laboratories, Inc., Okayama, Japan, 0.5 units/g starch of the above thermostable non-reducing saccharide-forming enzyme and 0.5 units/g starch of the above thermostable trehalose-releasing enzyme, and subjected to an enzymatic reaction for 96 hours. The resultant mixture was kept at 97° C. for 30 min, cooled and filtered. The resultant filtrate was in the usual manner decolored with an activated charcoal, and purified by desalting it with ion-exchange resins in H- and OH-form. The resultant solution was concentrated into a syrup with a concentration of about 60 w/v % in a yield of about 93%, d.s.b. The product contains 71.2% trehalose, 3.0% glucosyltrehalose, 1.3% maltosyltrehalose, 2.9% glucose, 11.1% maltose, 8.5% maltotriose, 2.0% maltooligosaccharides including higher molecular than maltotetraose and inclusive, d.s.b. The product has a mild and high-quality sweetness, as well as an adequate viscosity and moisture-retaining ability, and these properties render it arbitrarily useful in food products, cosmetics and pharmaceuticals as a sweetener, taste-improving agent, quality-improving agent, stabilizer and filler.

EXAMPLE A-2

A saccharide solution as a feed solution, obtained by the method in Example A-1, was fractionated by using a column packed with "XT-1016 (Na$^+$-form, polymerization degree of 4%)", a strong-acid cation exchange resin commercialized by Tokyo Organic Chemical Industries Ltd., Tokyo, Japan. The procedure was as follows: The resin was packed in 4-jacketed stainless steel columns having an inner diameter of 5.4 cm, and the columns were cascaded in series to give a total gel-bed depth of 20 m. The columns were heated to give the inner column temperature of 55° C. and fed with 5 v/v % of the saccharide solution against the resin while keeping at the temperature, followed by feeding to the columns with 55° C. hot water to fractionate the saccharide solution and to remove concomitant saccharides such as maltose and maltotriose, and recovering trehalose-rich fractions. The fractions thus obtained were pooled, purified, concentrated, dried in vacuo and pulverized to obtain a high trehalose content powder in a yield of about 57%, d.s.b. The content of trehalose in the product is about 97%, d.s.b., and the product has a mild and high-quality sweetness, and because of these it is arbitrarily used in food products, cosmetics and pharmaceuticals as a sweetener, taste-improving agent, quality-improving agent, stabilizer, excipient, diluent and filler.

EXAMPLE A-3

A high trehalose content fraction obtained by the method in Example A-2 was in a usual manner decolored with an activated charcoal, desalted with an ion-exchanger, and concentrated into an about 70% solution which was then placed in a crystallizer, admixed with about 2% hydrous crystalline trehalose as a seed crystal, and gradually cooled to obtain a massecuite with a crystallinity of about 45%. The massecuite was sprayed from a nozzle equipped at the top of a drying tower at a high pressure of 150 kg/cm². In the spraying step, the massecuite was simultaneously ventilated with 85° C. hot air being sent from the top of the drying tower, and the resultant crystalline powder was collected on a metal wire netting conveyer provided on the basement of the drying tower, and gradually moved out of the drying tower while a stream of 45° C. air was passing upwards through the metal wire netting. The resultant crystalline powder was injected in an ageing tower and aged for 10 hours to complete the crystallization and drying, followed by recovering a powdery hydrous crystalline trehalose in a yield of about 90% against the material high trehalose content fraction, d.s.b. The product is substantially non-hygroscopic and handles easily, and these render it arbitrarily useful in food products, cosmetics and pharmaceuticals as a sweetener, taste-improving agent, quality-improving agent, stabilizer, excipient, diluent and filler.

EXAMPLE A-4

A high trehalose content fraction obtained by the method in Example A-2 was purified similarly as in Example A-3, and the resultant was placed in an evaporator, and boiled up in vacuo to obtain a syrup with a moisture content of about 3.0%. The resultant syrup was placed in a crystallizer, admixed with one % anhydrous crystalline trehalose against the dry weight of the syrup, and crystallized at 120° C. for 5 min under stirring conditions, and the resultant mixture was placed in a plain aluminum-container and aged at 100° C. for 6 hours to obtain a block. The resultant block was pulverized by a cutter and dried by a fluidized-bed drying to obtain a powdery anhydrous crystalline trehalose with a moisture content of about 0.3% in a yield of about 85% against the material high trehalose content fraction, d.s.b. The product can be arbitrarily used as a desiccant in food products, cosmetics and pharmaceuticals, as well as their materials and intermediates. The product can be also used as a white powdery sweetener in a variety of compositions such as food products, cosmetics and pharmaceuticals.

EXAMPLE A-5

In accordance with the method in Example A-1, a seed culture of a mutant of *Sulfolobus acidocaldarius* (ATCC 33909) was incubated by a fermenter for about 42 hours. After completion of the incubation, the resultant cells were membrane filtered with an SF-membrane to recover an about 5 L filtrate which was treated with "MINI-LAB", a superhigh-pressure cell homogenizer, commercialized by Dainippon Pharmaceutical Co., to disrupt the cells. The resultant solution was centrifuged to recover about 4.8 L supernatant. To the resultant supernatant was added ammonium sulfate to give a supersaturation degree of about 0.7, and the resultant solution was salted out and centrifuged to obtain a precipitate. The precipitate was dissolved in 10 mM phosphate buffer (pH 6.5), and dialyzed against a fresh preparation of the same phosphate buffer to recover about 600 ml enzyme solution containing about 15 units/ml of thermostable non-reducing saccharide-forming enzyme and about 12 units/ml of thermostable trehalose-releasing enzyme, and followed by subjecting to a hydrophobic column chromatography to recover 5,850 units of thermostable non-reducing saccharide-forming enzyme and 3,960 units of thermostable trehalose-releasing enzyme. One part by weight of potato starch was admixed with 6 parts by weight of water and 0.01 part by weight of "NEO-SPITASE", α-amylase, commercialized by Nagase Biochemicals, Ltd., Kyoto, Japan. The resultant mixture was stirred and adjusted to pH 6.2, which was gelatinized and liquidized at a temperature of 85° to 90° C. The resultant liquidized solution was heated at 120° C. for 10 min to inactivate the remaining α-amylase, cooled to 60° C., adjusted to pH 5.5, admixed with 500 units/g starch of "PROMOZINE", pullulanase commercialized by Novo Nordisk Bioindustry, Copenhagen, Denmark, one unit/g starch of the above thermostable non-reducing saccharide-forming enzyme and one unit/g starch of the above thermostable trehalose-releasing enzyme, and subjected to an enzymatic reaction for 72 hours. The resultant mixture was heated at 97° C. for 30 min to inactivate the remaining enzymes, adjusted to 50° C. and pH 5.0, admixed with 10 units/g starch of "GLUCOZYME", glucoamylase commercialized by Nagase Biochemicals, Ltd., subjected to an enzymatic reaction for 24 hours, and heated to inactivate the enzyme. The resultant solution was, in a usual manner, decolored, desalted with ion-exchange resins and concentrated into a syrup with a concentration of about 60%. The saccharide solution thus obtained contained 79.5% trehalose, d.s.b. The saccharide solution was column chromatographed in accordance with the method in Example A-2 except that "CG 6000 (Na⁺-form)", a strongly-acidic cation exchange resin commercialized by Japan Organo Co., Ltd., Tokyo, Japan, was used as a resin for fractionation, followed by recovering a trehalose-rich fraction. The fraction contained about 95% trehalose, d.s.b., and it was concentrated into an about 75% solution which was then placed in a crystallizer, admixed with about 2% hydrous crystallized trehalose as a seed crystal and gradually crystallized under stirring conditions. The resultant was placed in a plain plastic-vessel and allowed to stand at an ambient temperature for 3 days to form a block. The resultant block was then pulverized by a cutter to obtain a powdery hydrous crystalline trehalose in a yield of about 70% against the material starch, d.s.b. The product is substantially non-hygroscopic and handles easily, and these render it arbitrarily useful in a variety of compositions such as food products, cosmetics and pharmaceuticals as a sweetener, taste-improving agent, quality-improving agent, stabilizer, excipient, diluent and filler.

EXAMPLE A-6

In accordance with the method in Experiment 1, a seed culture of *Sulfolobus solfatarius* (ATCC 35091) was incubated by a fermenter for about 42 hours. After completion of the incubation, in accordance with the method in Example A-1, the resultant cells were subjected to an SF-membrane filtration and a cell disruption. The resultant supernatant was salted out with ammonium sulfate to obtain a precipitate. The precipitate was dialyzed and followed by subjecting to an ion-exchange column chromatography to recover fractions with enzyme activity. The fractions were concentrated with an UF-membrane and followed by recovering about 150 ml concentrated enzyme solution containing 26.4 units/ml of thermostable non-reducing saccharide-forming enzyme and 57.5 units/ml of thermostable trehalose-releasing enzyme. The enzyme solution was subjected to a hydrophobic column chromatography to recover 2,650 units of thermostable non-reducing saccharide-forming enzyme and 5,950 units of thermostable trehalose-releasing enzyme. The suspension of potato starch having a concentration of 6% was gelatinized by heating, adjusted to pH 4.5 and 50° C., admixed with 500 units/g starch of isoamylase, and subjected to an enzymatic reaction for 20 hours. The resultant mixture was adjusted to pH 6.5, autoclaved at 120° C. for 10 min, cooled to 95° C., admixed with 0.1 w/w % per g starch of "TERMAMYL 60L", α-amylase commercialized by Novo Industri A/S, Copenhagen, Denmark, and subjected to an enzymatic reaction for 15 min. The reaction mixture was autoclaved at 130° C. for 30 min, cooled to 65° C., admixed with one unit/g starch of the above non-reducing saccharide-forming enzyme and one unit/g starch of the above trehalose-releasing enzyme, and subjected to an enzymatic reaction for 72 hours. The resultant mixture was kept at 97° C. for 30 min, adjusted to pH 5.0 and 50° C., admixed with 10 units/g starch of "GLUCOZYME", glucoamylase commercialized by Nagase Biochemicals, Ltd., subjected to an enzymatic reaction for 24 hours, and heated to inactivate the enzyme. The resultant solution was, in a usual manner, decolored, desalted with ion-exchange resins and concentrated into a syrup with a concentration of about 60%. The saccharide solution thus obtained contained 80.9% trehalose, d.s.b. The saccharide solution was concentrated to give a concentration of about 84%, and then placed in a crystallizer, admixed with about 2% hydrous crystalize trehalose as a seed crystal and gradually crystallized under stirring conditions. The resultant was placed in a plain plastic-vessel and allowed to stand at an ambient temperature for 3 days to form a block. The resultant block was then pulverized by a cutter to obtain a powdery hydrous crystalline trehalose in a yield of about 90% against the material starch, d.s.b. The product is substantially non-hygroscopic and handles easily, and these render it arbitrarily useful in a variety of compositions such as food products, cosmetics and pharmaceuticals as a sweetener, taste-improving agent, quality-improving agent, stabilizer, excipient, diluent and filler.

EXAMPLE B-1

Sweetener

To one part by weight of a powdery hydrous crystalline trehalose, obtained by the method in Example A-3, were homogeneously added 0.01 part by weight of "αG SWEET", an α-glycosyl stevioside product commercialized by Toyo Sugar Refining Co., Ltd., Tokyo, Japan, and 0.01 part by weight of "ASPARTAME", an L-aspartyl-L-phenylalanine methylester product commercialized by Ajinomoto Co., Ltd., Tokyo, Japan, and the resultant mixture was fed to a granulator to obtain a granular sweetener. The product has a satisfactory sweetness and an about 2.5-fold higher sweetening power of sucrose, and the caloric value is about 1/2.5 of that of sucrose. The product having a satisfactory stability does not decompose other sweeteners to be mixed, and with which it is suitably used as a low-caloric sweetener for low-caloric food products directed to fat persons and diabetics who are restricted to a reduced calorie intake. The product substantially does not form insoluble glucans, and this renders it useful for sweetening food products to prevent dental caries.

EXAMPLE B-2

Hard candy

One hundred parts by weight of 55% sucrose solution was mixed while heating with 30 parts by weight of a trehalose syrup, obtained by the method in Example A-1, and the resultant solution was concentrated in vacuo until the moisture content decreased to below 2%. The concentrated solution was admixed with one part by weight of citric acid and adequate amounts of a lemon flavor and a coloring agent, and the resultant mixture was in a usual manner formed into the desired product. The product is a high-quality hard candy having a satisfactory taste and biting property, as well as having no fear of causing crystallization of sucrose.

EXAMPLE B-3

Chewing gum

Three parts by weight of a gum base was melted by heating until it softened, and the resultant was mixed with 4 parts by weight of sucrose and 3 parts by weight of a hydrous crystalline trehalose powder obtained by the method in Example A-3, and further mixed with adequate amounts of a flavor and a coloring agent. The resultant mixture was in usual manner kneaded by a roll, formed and packed to obtain the desired product. The product is a chewing gum having a satisfactory texture and taste.

EXAMPLE B-4

Sweetened condensed milk

Three parts by weight of a trehalose syrup obtained by the method in Example A-1 and one part by weight of sucrose were dissolved in 100 parts by weight of fresh milk, and the resultant solution was sterilized by heating with a plate heater, and condensed to give a concentration of 70%, followed by aseptically canning the resultant concentrate into the desired product. The product has a mild sweetness and a satisfactory taste, and these render it arbitrarily useful as a seasoning for baby foods, foods for infants, fruit, coffee, cocoa and tea.

EXAMPLE B-5

Beverage containing lactic acid bacteria

One hundred and seventy-five parts by weight of defatted milk, 130 parts by weight of a trehalose syrup prepared by the method in Example A-1, and 50 parts by weight of a high lactosucrose content powder disclosed in Japanese Patent Laid-Open No. 281,795/92 were dissolved in 1,150 parts by weight of water, and the resultant solution was sterilized by heating at 65° C. for 30 min, cooled to 40° C., admixed in usual manner with 30 parts by weight of lactic acid bacteria as a starter, and incubated at 37° C. for 8 hours to obtain a beverage containing lactic acid bacteria. The product is a beverage containing lactic acid bacteria with a satisfactory taste and flavor. The product containing oligosaccharides stably retains lactic acid bacteria and promotes the growth of bifid bacteria.

EXAMPLE B-6

Powdered juice

Thirty-three parts by weight of a powdered orange juice prepared by spray drying was mixed to homogeneity with 50 parts by weight of a high trehalose content powder obtained by the method in Example A-2, 10 parts by weight of sucrose, 0.65 parts by weight of anhydrous citric acid, 0.1 part by weight of malic acid, 0.1 part by weight of L-ascorbic acid, 0.1 part by weight of sodium citrate, 0.5 parts by weight of pullulan, and an adequate amount of a powdered flavor. The resultant mixture was pulverized, fed to a fluidized-bed granulator and sprayed with a trehalose syrup as a binder obtained by the method in Example A-1 while sending to the contents 40° C. air at a flow rate of 150 m³. The granules thus obtained were weighed and packaged to obtain the desired product. The product containing 30% orange juice, d.s.b., retains its high quality for a relatively-long period of time without giving an unsatisfactory taste and smell.

EXAMPLE B-7

Custard cream

One hundred parts by weight of corn starch, 100 parts by weight of a trehalose syrup obtained by the method in Example A-1, 80 parts by weight of maltose, 20 parts by weight of sucrose, and one part by weight of salt were mixed to homogeneity. The resultant mixture was admixed with 280 parts by weight of egg, and gradually added with 1,000 parts by weight of a boiling milk. The mixture thus obtained was continuously stirred while heated, and the heating was stopped when the corn starch in the mixture was completely gelatinized to render the whole contents semitransparent, followed by cooling the mixture and adding thereto an adequate amount of a vanilla flavor. The resultant mixture was weighed, injected and packaged to obtain the desired product. The product has a smooth surface and gloss, as well as a mild taste and sweetness.

EXAMPLE B-8

Uiro-no-moto (an instant mix for uiro)

Ninety parts by weight of rice powder was admixed to homogeneity with 20 parts by weight of corn starch, 40 parts by weight of sucrose, 80 parts by weight of a powder containing hydrous crystalline trehalose obtained by the method in Example A-3 and 4 parts by weight of pullulan to obtain "uiro-no-moto". The "uiro-no-moto" was kneaded with appropriate amounts of "maccha (a green tea powder)" and water and the resultant mixture was divided in vessels and steamed for 60 minutes to obtain "maccha-uiro". The product has a smooth gloss, good palatability and delicious taste, and also has a long shelf life because retrogradation of starch effectively suppressed.

EXAMPLE B-9

An (beans paste)

Ten parts by weight of "adzuki" beans as a material was boiled by the addition of water in usual manner, followed by removing the astringency and harshness of the beans, as well as water-soluble impurities, to obtain about 21 kg "adzuki-tsubu-an". To the resultant was added 14 parts by weight of sucrose, 5 parts by weight of a trehalose syrup obtained by the method in Example A-1, and 4 parts by weight of water, and the resultant mixture was boiled, admixed with a small amount of salad oil, and carefully kneaded up so as not to paste the beans. Thus, the desired product was obtained in a yield of about 35 kg. The product free from discoloration induced by boiling has a satisfactory taste and flavor, and these render it useful as a material "an" for bean-jam buns, buns with bean-jam filling, dumplings, bean-jam-filled wafers, sherbets and ice creams.

EXAMPLE B-10

Bread

One hundred parts by weight of wheat powder, 2 parts by weight of yeast, 5 parts by weight of sugar, one part by weight of a powder containing trehalose obtained by the method in Example A-2, 0.1 part by weight of inorganic yeast food were kneaded with water in usual manner to effect fermentation at 26° C. for 2 hours, and further aged for 30 min, followed by baking the resultant. The product is a high-quality bread having a satisfactory hue and rising, as well as a satisfiable elasticity and mild sweetness.

EXAMPLE B-11

Ham

To one thousand parts by weight of ham meat slices was added and ground to homogeneity 15 parts by weight of salt and 3 parts by weight of potassium nitrate, and the resultant slices were piled up and allowed to stand overnight in a cold-storage room. Thereafter, the resultant slices were first soaked for 7 days in a cold-storage room in a salt solution consisting of 500 parts by weight of water, 100 parts by weight of salt, 3 parts by weight of potassium nitrate, 40 parts by weight of a powdery hydrous crystalline trehalose prepared by the method in Example A-6, and an adequate amount of a peppermint, then washed with cold water in usual manner, tied up, smoked, cooked, cooled and packaged to obtain the desired product. The product is a high-quality ham having a satisfactory hue, taste and flavor.

EXAMPLE B-12

Powdery peptide

One part by weight of 40% "Hinute S", a peptide solution of edible soy beans commercialized by Fuji Oil Co., Ltd., Tokyo, Japan, was admixed with 2 parts by weight of a powdery hydrous crystalline trehalose prepared by the method in Example A-6, and the resultant mixture was placed in a plastic vessel, dried in vacuo at 50° C., and pulverized to obtain a powdery peptide. The product having a satisfactory taste and flavor can be arbitrarily used as a material for confectioneries such as premixes, sherbets and ice creams, as well as baby foods and therapeutic nutrition in the form of oral and intubation feedings.

EXAMPLE B-13

Powdered miso

To one part by weight of "akamiso" (a kind of miso) was added 3 parts by weight of a powdery anhydrous crystalline trehalose obtained by the method in Example A-4, and the mixture was poured into a metal plate having hemisphere wells on its surface and allowed to stand at an ambient temperature overnight to obtain "miso" solids, about 4 g weight each, which were then subjected to a pulverizer to obtain the desired product. The product can be arbitrarily used as a seasoning for instant noodles and soups, as well as a "miso" confectionery.

EXAMPLE B-14

Powdery egg yolk

Egg yolks prepared from fresh eggs were sterilized at 60°–64° C. by a plate heater, and the resultant liquid was admixed with 4 parts by weight of a powdery anhydrous crystalline trehalose prepared by the method in Example A-4 with respect to one part by weight of the liquid. The resultant mixture was transferred to a vessel, allowed to stand overnight to form a block while the anhydrous crystalline trehalose was allowed to convert into hydrous crystalline trehalose. The block thus obtained was pulverized by a cutting machine to obtain a powdery egg yolk. The product can be arbitrarily used as a material for confectioneries for premixes, sherbets, ice cream and emulsifiers, as well as baby foods and therapeutic nutrition in the form of oral and intubation feedings. The product can be also used as a skin refiner and hair restorer.

EXAMPLE B-15

Cosmetic cream

Two parts by weight of polyoxyethylene glycol monostearate, 5 parts by weight of glyceryl monostearate, self-emulsifying, 2 parts by weight of a high trehalose content powder obtained by the method in Example A-2, one part by weight of α-glycosyl rutin, one part by weight of liquid petrolatum, 10 parts by weight of glyceryl tri-2-ethylhexanoate, and an adequate amount of an antiseptic were in usual manner dissolved by heating. The resultant solution was admixed with 2 parts by weight of L-lactic acid, 5 parts by weight of 1,3-butylene glycol and 66 parts by weight of refined water, and the resultant mixture was emulsified by a homogenizer and admixed with an adequate amount of a flavor under stirring conditions to obtain a cosmetic cream. The product exhibits an antioxidant activity and has a relatively-high stability, and these render it arbitrarily useful as a high-quality sunscreen, skin-refining agent and skin-whitening agent.

EXAMPLE B-16

Powdery ginseng extract

A half part by weight of ginseng extract was mixed with 1.5 parts by weight of a powdery anhydrous crystalline trehalose prepared by the method in Example A-4, and the resultant mixture was transferred to a plain container, allowed to stand for 2 days to convert anhydrous crystalline trehalose into hydrous crystalline trehalose to form a block. The resultant block was pulverized by a cutter and classified to obtain a powdery ginseng extract. The product and adequate amounts of powdery vitamins B1 and B2 were subjected to a granulator to obtain a powdery ginseng extract containing vitamins. The product thus obtained can be arbitrarily used as a tonic, fatigue-relieving agent and vitality-imparting agent. The product can be also used as a hair restorer.

EXAMPLE B-17

Solid pharmaceutical

A natural human interferon-α preparation, commercialized by Hayashibara Biochemical Laboratories, Inc., Okayama, Japan, was in usual manner fed to a column of an immobilized anti-human interferon-α antibody to adsorb the natural human interferon-α, and a buffer containing calf serum albumin as a stabilizer was fed to the column, followed by removing an excessive amount of the albumin. Thereafter, the interferon-α was eluted from the column with a physiological saline containing 5% powder rich in trehalose, prepared by the method in Example A-2, while the pH of the physiological saline was varying. The resultant eluate was membrane filtered, and the filtrate was dehydrated by the addition of about 20-fold volumes of "FINETOSE®", an anhydrous crystalline maltose powder commercialized by Hayashibara Shoji, Inc., Okayama, Japan, followed by pulverizing the resultant dehydrated product, and tabletting the resultant powder by a tabletting machine to obtain tablets containing about 150 units of the natural human interferon-α per one tablet, about 200 mg weight. The product can be orally administered as a sublingual tablet to patients at a dose of 1–10 tablets/adult/day, and arbitrarily used to treat vital diseases, allergies, rheumatisms, diabetes and malignant tumors. More particularly, the product can be suitably used as a therapeutic agent for AIDS and hepatitis, the number of patients suffering from these diseases has been remarkably increased. The trehalose and maltose incorporated in the product act as a stabilizer for the natural human interferon-α, so that the activity is well retained for a relatively-long period of time even at an ambient temperature.

EXAMPLE B-18

Sugar coated tablet

A crude tablet as a core, 150 mg weight, was coated with a solution consisting of 40 parts by weight of a powdery hydrous crystalline trehalose obtained by the method in Example A-3, 2 parts by weight of pullulan having an average molecular weight of 200,000, 30 parts by weight of water, 25 parts by weight of talc, and 3 parts by weight of titanium oxide until the total weight reached to about 230 mg, and the resultant was further coated with a solution consisting of 65 parts by weight of a fresh preparation of the same powdery hydrous crystalline trehalose, one part by weight of pullulan, and 34 parts by weight of water, and glossed with a liquid wax to obtain a sugar coated tablet having a satisfactory gloss and appearance. The product has a relatively-high shock tolerance and retains its high quality for a relatively-long period of time.

EXAMPLE B-19

Dentifrice

| Composition: | |
|---|---|
| calcium hydrogen phosphate | 45.0% |
| pullulan | 2.95% |
| sodium laurate | 1.5% |
| glycerine | 20.0% |
| polyoxyethylene sorbitan laurate | 0.5% |
| antiseptic | 0.05% |
| powdery hydrous crystalline trehalose, obtained by the method in Example A-3 | 12.0% |
| maltitol | 5.0% |
| water | 13.0% |

The above materials were mixed in usual manner to obtain dentifrice. The product, having an adequate sweetness, is suitable as dentifrice for a child.

EXAMPLE B-20

Intubation feeding

A composition consisting of 500 parts by weight of a powdered hydrous crystalline trehalose obtained by the method in Example A-3, 270 parts by weight of dried yolk, 209 parts by weight of defatted milk, 4.4 parts by weight of sodium chloride, 1.8 parts by weight of potassium chloride, 4 parts by weight of magnesium sulfate, 0.01 part by weight of thiamine, 0.1 part by weight of sodium ascorbate, 0.6 parts by weight of vitamin E acetate and 0.04 parts by weight of nicotine amide was prepared, and the composition was divided into 25 g aliquot in small moistureproof laminated aluminum packs which were then heat-sealed. One pack of the product is dissolved in about 150–300 ml water and the resultant solution is usable as an a liquid supplemental nutrition parenterally administrable to the nasal cavity, stomach or intestine.

EXAMPLE B-23

Traumatic oniment

Two hundred parts by weight of powdered hydrous crystalline trehalose obtained by the method in Example A-3 and 300 parts by weight of maltose were admixed with 50 parts by weight of methanol containing 3 parts by weight of iodine, and the resultant was mixed with 200 parts by weight of 10 w/v % pullulan to obtain a traumatic ointment which has an appropriate extensity and adhesiveness. The product shortens a therapeutic period and cures traumas without a scar by reason that the iodine incorporated in the product exhibits sterilizing effects and also the trehalose incorporated in the product supplements nutrition into traumas.

As is evident from above, the present novel thermostable trehalose-releasing enzyme releases trehalose from non-reducing saccharides having a trehalose structure as an end unit and having a degree of glucose polymerization of 3 or higher, is superior in thermal stability, and forms trehalose in a relatively-high yield when acted on reducing partial starch gives an unfathomable great influence on the fields such as starch-, enzyme- and biochemical-sciences, and other industrial fields, especially, food-, cosmetic- and pharmaceutical-industries, as well as forestry, fisheries, and agricultural-, livestock- and chemical-industries. Thus, the influence of the present invention on these fields is unfathomably great.

While there has been described what is at present considered to be the preferred embodiments of the invention, it will be understood the various modifications may be made therein, and it is intended to cover in the appended claims all such modifications as fall within the true spirit and scope of the invention.

---

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 10 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Met Phe Ser Phe Gly Gly Asn Ile Gln Lys
   1               5                   10

(2) INFORMATION FOR SEQ ID NO:2:

(i) SEQUENCE CHARACTERISTICS:
      (A) LENGTH: 10 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

Met Ile Ser Ala Thr Trp Arg Leu Gln Leu
   1               5                   10

--- hydrolysates together with a thermostable non-reducing saccharide-forming enzyme. The trehalose thus obtained can be readily separated and purified, and the resultant purified trehalose and saccharide compositions containing the same have a satisfactory stability as well as a relatively-high quality and moderate sweetness. Since trehalose can be readily assimilated and absorbed by living bodies when orally taken, the product can be used as energy source, and the product per se and saccharide compositions containing the same can be arbitrarily used as a sweetener, taste-improving agent, quality-improving agent, stabilizer, excipient, diluent and filler in a variety of compositions such as food products, cosmetics and pharmaceuticals.

Thus, the present invention provides a novel technique to prepare trehalose and saccharide compositions containing the same in an industrial-scale and relatively-low cost from partial starch hydrolysates prepared from starch, a cheap and abundant natural source. Therefore, the present invention

We claim:

1. A purified trehalose-releasing enzyme which specifically hydrolyses the linkage between a trehalose moiety and the remaining glycosyl moiety in a non-reducing saccharide having a trehalose structure as an end unit and a degree of glucose polymerization of at least 3 and which enzyme is capable of acting on the non-reducing saccharide at a temperature of over 55° C. while retaining its activity.

2. The enzyme of claim 1, wherein said glycosyl moiety consists of one or more glucose residues.

3. The enzyme of claim 1, which retains its activity up to a temperature of about 85° C. when incubated at pH 7.0 for 60 min.

4. The enzyme of claim 1, which is derived from a microorganism.

5. The enzyme of claim 4, wherein said microorganism is a member selected from the group consisting of those of the genus Sulfolobus and mutants thereof.

6. The enzyme of claim 1, which has the following physicochemical properties:

(1) Action

Specifically hydrolyzing the linkage between a trehalose moiety and the remaining glycosyl moiety in a non-reducing saccharide having a trehalose structure as an end unit and a degree of glucose polymerization of at least 3;

(2) Molecular weight

About 54,000 to 64,000 daltons on sodium dodecyl sulfate polyacrylamide gel electrophoresis (SDS-PAGE);

(3) Isoelectric point (pI)

About 5.6 to 6.6 on isoelectrophoresis using ampholyte;

(4) Optimum temperature

About 75° C. when incubated at pH 6.0 for 30 min;

(5) Optimum pH

About 5.5 to 6.0 when incubated at 60° C. for 30 min;

(6) Thermal stability

Retains its stability up to a temperature of about 85° C. when incubated at pH 7.0 for 60 min; and (7) pH stability Retains its stability at a pH of about 4.0 to 9.5 when incubated at 25° C. for 16 hours.

7. A process for preparing the enzyme of claim 1, which comprises culturing in a nutrient culture medium a microorganism capable of producing said enzyme, and recovering the said enzyme from the resultant culture.

8. The process of claim 7, wherein said microorganism is a member selected from the group consisting of those of the genus Sulfolobus and mutants thereof.

9. A process for preparing trehalose which contains a step of allowing the enzyme of claim 1 to act on a solution containing a non-reducing saccharide having a trehalose structure as an end unit and a degree of glucose polymerization of at least 3.

10. The process of claim 9, wherein a non-reducing saccharide-forming enzyme is allowed to act on a solution containing one or more reducing partial starch hydrolysates together with the enzyme of claim 1.

11. The process of claim 9, wherein said trehalose is a member selected from the group consisting of hydrous crystalline trehalose, anhydrous crystalline trehalose, and mixture thereof.

12. A process for preparing a saccharide composition comprising:

(a) contacting a solution containing a non-reducing saccharide having a trehalose structure as an end unit and a degree of glucose polymerization of at least 3 with the enzyme of claim 1 to produce trehalose; and (b) incorporating trehalose obtained in step (a) into at least one other saccharide.

13. A process for preparing a food product comprising:

(a) contacting a solution containing a non-reducing saccharide having a trehalose structure as an end unit and a degree of glucose polymerization of at least 3 with the enzyme of claim 1 to produce trehalose; and (b) incorporating trehalose obtained in step (a) into a food material.

14. A process for preparing a cosmetic composition comprising:

(a) contacting a solution containing a non-reducing saccharide having a trehalose structure as an end unit and a degree of glucose polymerization of at least 3 with the enzyme of claim 1 to produce trehalose; and (b) incorporating trehalose obtained in step (a) into a cosmetically-acceptable carrier.

15. A process for preparing a pharmaceutical composition comprising:

(a) contacting a solution containing a non-reducing saccharide having a trehalose structure as an end unit and a degree of glucose polymerization of at least 3 with the enzyme of claim 1 to produce trehalose; and (b) incorporating trehalose obtained in step (a) into a pharmaceutically-acceptable carrier.

* * * * *